United States Patent
Wooley et al.

(10) Patent No.: US 9,016,859 B2
(45) Date of Patent: Apr. 28, 2015

(54) PRESBYOPIA LENS WITH PUPIL SIZE CORRECTION BASED ON LEVEL OF REFRACTIVE ERROR

(71) Applicant: Johnson & Johnson Vision Care, Inc., Jacksonville, FL (US)

(72) Inventors: C. Benjamin Wooley, Jacksonville, FL (US); James William Haywood, Fleming Island, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 61 days.

(21) Appl. No.: 13/828,012

(22) Filed: Mar. 14, 2013

(65) Prior Publication Data
US 2014/0268034 A1 Sep. 18, 2014

(51) Int. Cl.
*G02C 7/04* (2006.01)
*G02C 7/02* (2006.01)
*A61F 2/16* (2006.01)

(52) U.S. Cl.
CPC ........... *G02C 7/028* (2013.01); *G02C 7/027* (2013.01); *A61F 2/1613* (2013.01); *G02C 7/024* (2013.01); *G02C 7/04* (2013.01); *G02C 7/044* (2013.01)

(58) Field of Classification Search
CPC ......... G02C 7/024; G02C 7/027; G02C 7/028
USPC ............ 351/159.02, 159.07, 159.22, 159.46, 351/159.52, 159.74, 159.77, 159.78
See application file for complete search history.

(56) References Cited

U.S. PATENT DOCUMENTS

| | | | |
|---|---|---|---|
| 5,929,969 A | 7/1999 | Roffman | |
| 2007/0258042 A1 | 11/2007 | Wooley et al. | |
| 2009/0059167 A1 | 3/2009 | Wooley et al. | |
| 2009/0066913 A1* | 3/2009 | Dai et al. | 351/177 |

FOREIGN PATENT DOCUMENTS

EP 0742464 A2 11/1996

OTHER PUBLICATIONS

Partial European Search Report dated Jun. 18, 2014 for Application No. EP14160102.
European Search Report completed Oct. 17, 2014 for corresponding Application No. EP 14160102.

* cited by examiner

*Primary Examiner* — Darryl J Collins
(74) *Attorney, Agent, or Firm* — Carl J. Evens

(57) ABSTRACT

Ophthalmic lenses for the treatment of presbyopia may be improved to enhance the visual experience of the patient. By adjusting the optical design of presbyopic lenses to account for changes in pupil size due to the degree of myopia or hyperopia, an enhanced visual experience may be achieved independent of the level of ametropia.

16 Claims, 33 Drawing Sheets

Contact Lens Power Profile for "Nominal" Design

Contact Lens Power Profile for "Nominal" Design

Presbyope Pupil Data 250 cd/m$^2$

Prior Art 250 cd/m²

Scaling Method 250 cd/m²

Optimization Method 250 cd/m²

Prior Art 50 cd/m²

Scaling Method 50 cd/m²

Optimization Method 50 cd/m²

Prior Art 2.5 cd/m²

Scaling Method 2.5 cd/m²

Optimization Method 2.5 cd/m²

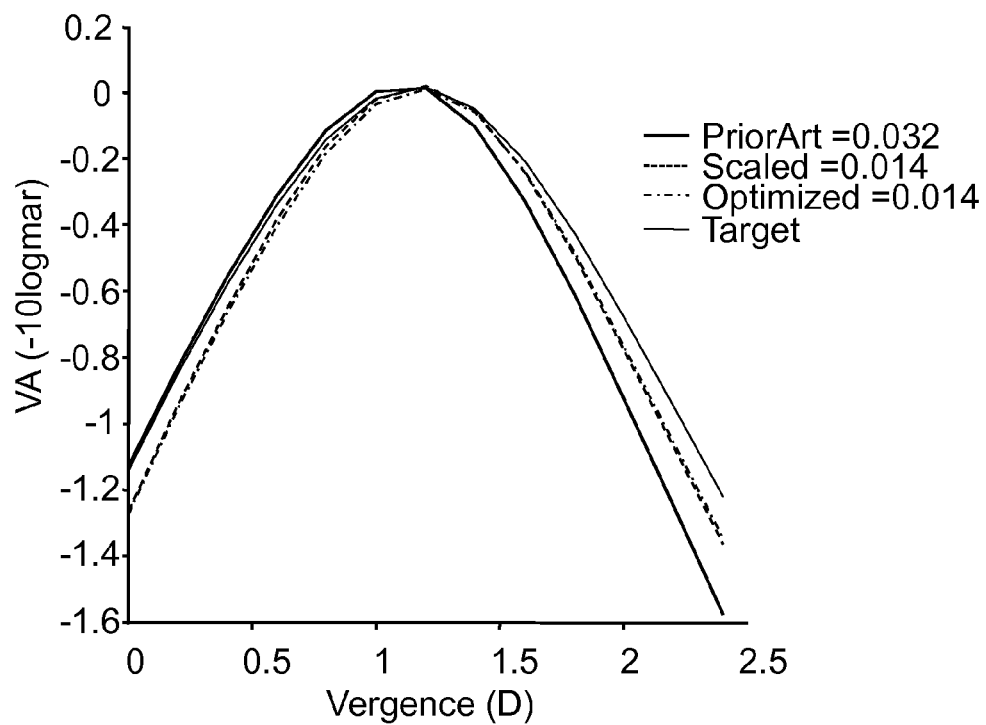
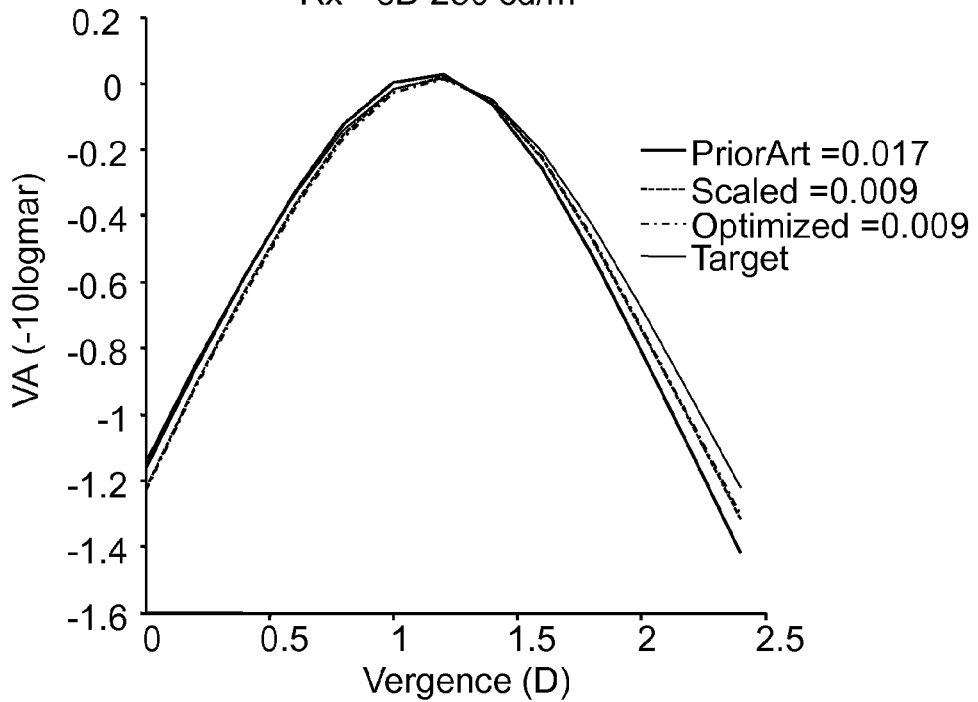

Rx=-3D 250 cd/m²

Rx=0D 250 cd/m²

Rx=-9D 50 cd/m²
— PriorArt =0.086
--- Scaled =0.032
-·-· Optimized =0.025
— Target Rx=-6D 50 cd/m²
— PriorArt =0.055
--- Scaled =0.021
-·-· Optimized =0.016
— Target Rx=-3D 50 cd/m²
— PriorArt =0.027
--- Scaled =0.01
-·-· Optimized =0.008
— Target

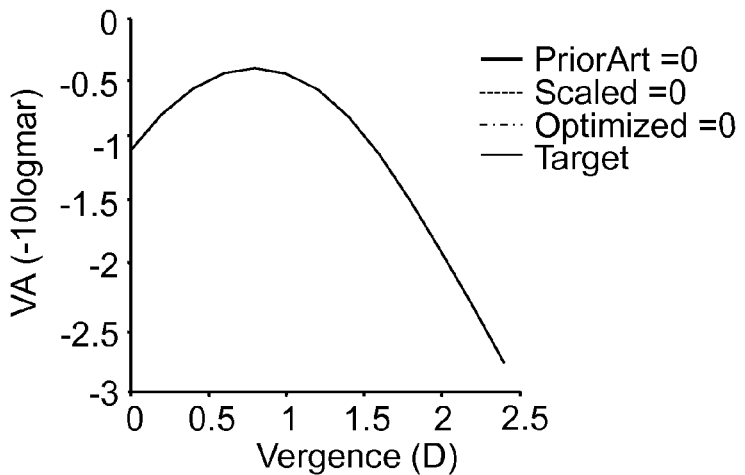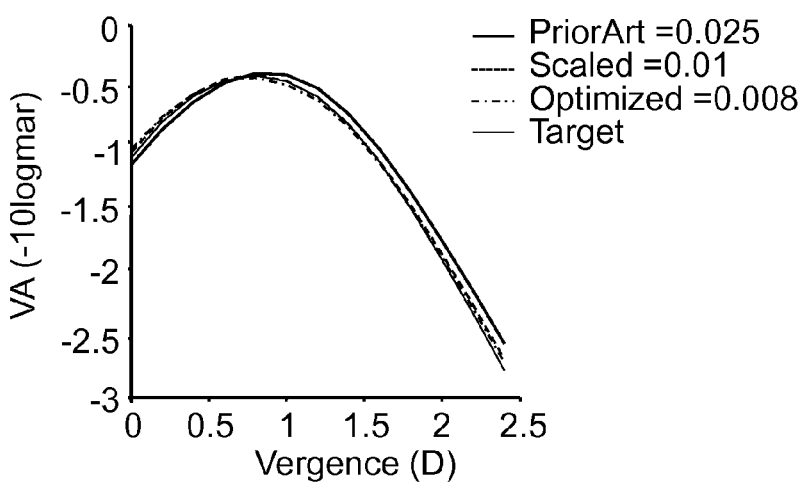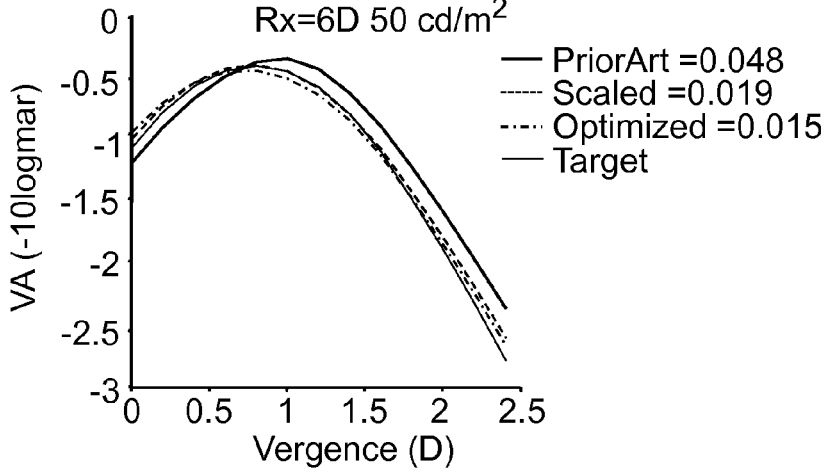

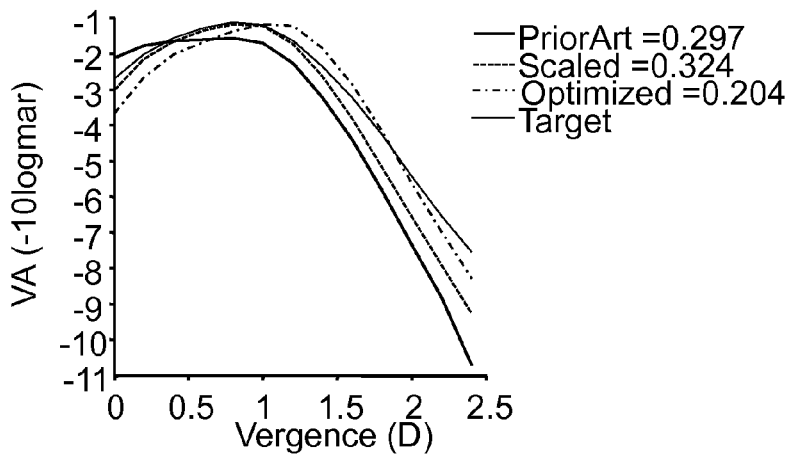
FIG. 12A₁
Rx=-9D 2.5 cd/m²
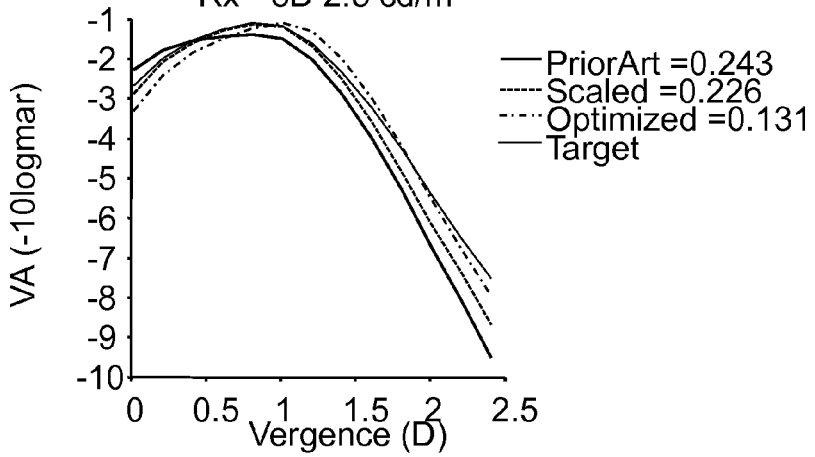
FIG. 12B₂
Rx=-6D 2.5 cd/m²
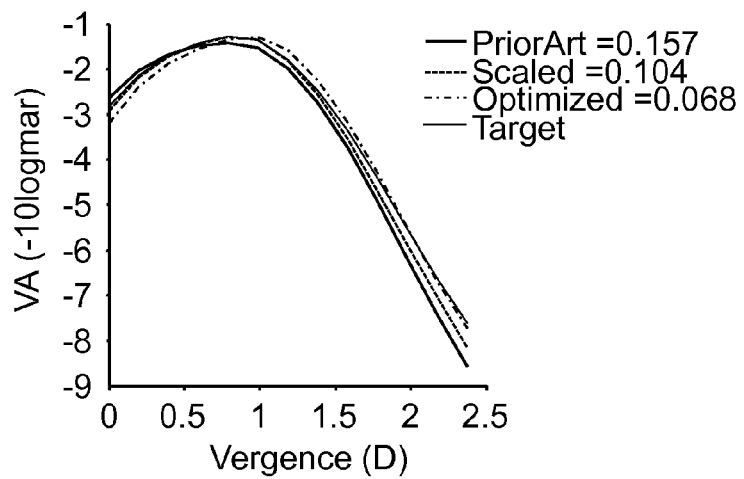
FIG. 12C₂
Rx=-3D 2.5 cd/m²

Rx=0D 2.5 cd/m²

Rx=3D 2.5 cd/m²

Rx=6D 2.5 cd/m²

Contact Lens Power Profile for Select SKUs - Optimization Method

Contact Lens Power Profile for Select SKUs - Scaling Method

Contact Lens Power Profile for Select
SKUs - Scaling Method

Contact Lens Power Profile for Select
SKUs - Optimization Method

Prior Art 250 cd/m²

Scaling Method 250 cd/m²

Optimization Method 250 cd/m²

Prior Art 50 cd/m²

Scaling Method 50 cd/m²

Optimization Method 50 cd/m²

Prior Art 2.5 cd/m²

Scaling Method 2.5 cd/m²

Optimization Method 2.5 cd/m²

Rx=-9D 250 cd/m²

Rx=-6D 250 cd/m²

Rx=-3D 250 cd/m²

Rx=0D 250 cd/m²

Rx=3D 250 cd/m²

Rx=6D 250 cd/m²

Rx=0D 50 cd/m²
— PriorArt =0
---- Scaled =0
-·-· Optimized =0.00011
— Target

Rx=3D 50 cd/m²
— PriorArt =0.0111
---- Scaled =0.00939
-·-· Optimized =0.00878
— Target Rx=6D 50 cd/m²
— PriorArt =0.0209
---- Scaled =0.0179
-·-· Optimized =0.0169
— Target Rx=-9D 2.5 cd/m²
— PriorArt =0.397
---- Scaled =0.556
-·- Optimized =0.272
— Target Rx=-6D 2.5 cd/m²
— PriorArt =0.294
---- Scaled =0.419
-·- Optimized =0.182
— Target Rx=-3D 2.5 cd/m²
— PriorArt =0.169
---- Scaled =0.222
-·- Optimized =0.0868
— Target Rx=0D 2.5 cd/m²
— PriorArt =0
---- Scaled =7.73e-16
-·-· Optimized =0.000234
— Target Rx=3D 2.5 cd/m²
— PriorArt =0.182
---- Scaled =0.177
-·-· Optimized =0.0639
— Target Rx=6D 2.5 cd/m²
— PriorArt =0.362
---- Scaled =0.343
-·-· Optimized =0.132
— Target Contact Lens Power Profile for Select SKUs

PRESBYOPIA LENS WITH PUPIL SIZE CORRECTION BASED ON LEVEL OF REFRACTIVE ERROR

BACKGROUND OF THE INVENTION

1. Field of the Invention

The present invention relates to contact lenses for correcting presbyopia, and more particularly to contact lenses for correcting presbyopia that are scaled based upon pupil size as it relates to refractive error to ensure that the design provides the same visual experience independent of the level of ametropia or refractive error. The present invention also relates to a method for adjusting the optical designs for lenses for correcting presbyopia to account for changes in pupil size as it relates to ametropia.

2. Discussion of the Related Art

As individuals age, their eyes are less able to accommodate, or bend their natural or crystalline lens, to focus on objects that are relatively near to the observer. This condition is known as presbyopia. More specifically, when an individual is born, the crystalline lens is pliable which makes it capable of a high degree of accommodation. As the individual ages, the crystalline lens gradually becomes more rigid and thus less able to accommodate. Similarly, for persons who have had their natural or crystalline lens removed and an intraocular lens or IOL inserted as a replacement, the ability to accommodate is absent. Although the intent of an accommodating IOL is to address this potential shortcoming, current accommodating IOL designs and concepts are relatively new and continue to evolve.

Various classes of contact lens and intra-ocular designs have been offered for the treatment of presbyopia. These include bi-focal and multi-focal contact lenses of various forms, including concentric rings, aspheric designs, as well as diffractive designs. These designs are typically depicted in the patent literature by their power profiles. Even if described by surface or other attributes, the power profile for a given design may be determined.

An example of a power profile for a concentric ring type design is illustrated in FIG. 1. The horizontal axis shows the radial position from the center of the lens in millimeters. The vertical axis shows the contact lens power, in diopters (D), relative to the label power of the contact lens. This particular design consists of five concentric rings. The contact lens power plotted here is relative to the label power. The label power is the power required to compensate for the level of ametropia or refractive error of the patient. For example, it may be determined by an eye care professional that an individual with myopia or nearsightedness requires −2.75 D lens to correct their ametropia. The label power of the contact lens selected will be −2.75 D.

For a particular design, such as the one illustrated in FIG. 1, there is required a set of lenses of a range of label powers. Typically a particular design such as the one illustrated in FIG. 1 is provided with label powers from −12.00 D to 8.00 D in 0.25 D increments. The prior-art (patent or otherwise) typically describes an optical design intended for the treatment of presbyopia for a single label power. The method for determining the designs at other label powers is not specified but implied in the description of the design at the nominal power. The implied method for the design from FIG. 1 to create the set of designs to cover a range of label powers is to take the nominal design and add to it a constant power equal to the label power. The set of power profiles for this design in 1.0 D increments from −8.0 D to +6.0 D label powers is illustrated in FIG. 2.

There are many forms of bi-focal or multi-focal contact lenses for the correction of presbyopia. These design forms include concentric rings, aspheric designs, as well as diffractive designs. All of these designs function by providing a range of powers within the pupil of the eye. For example, a concentric ring design may have a central ring that provides powers that are nominally equal to the power required to correct the distance vision of the subject, an adjacent ring that provides near powers, and an outer ring that also provides distance powers. There may also be versions or variations with intermediate powers to address situations between near and far distances, for example, computer screen viewing. An aspheric design may be considered a multi-focal or progressive type design that provide powers for a given pupil size that gradually change from being plus to distance in the center of the lens and providing powers for near vision correction to having distance powers at the edge of the pupil to provide distance vision correction.

Pupil size depends upon a number of factors, including light level. Much of the design work and prior art for presbyopic designs is concerned with optimizing the design performance for a range of light levels and thus pupil sizes. In designing these lenses for presbyopes, the pupil size is taken into account. The approach to doing this depends upon the intent of the design. One goal may be to make a design independent of pupil size so that vision will stay constant as light levels change and pupil sizes change. Alternatively, the intent may be to provide a lens that gives preference to near vision for small pupils and distance vision for large pupils such as is done by many of the center near designs. Or, the intent may be to provide a lens that gives preference to distance vision for small pupils and near vision for large pupils such as is done by many of the center distance designs. The design possibilities and permutations are essentially endless.

Pupil size also depends upon the level of ametropia. Referring now to FIGS. 3, 4 and 5, there is illustrated in graphical format the relationship between pupil size and refractive error for a given luminance level. More specifically, FIGS. 3-5 illustrated pupil size data collected at 2.5, 50, and 250 cd/m$^2$ (candela per square meter) luminance levels. This data is for subjects greater than forty (40) years old representing the presbyopic population. The pupil size data on the vertical axis is plotted against the refractive error in Diopters on the horizontal axis. As may be seen from the figures, the pupil sizes at all light levels are smaller for hyperopes than for myopes. Accordingly, since the pupil size at a given light level varies with the refractive error, then lenses for the treatment of presbyopia are needed that have their designs scaled based upon pupil size to ensure that the designs perform consistently independent of the refractive error being corrected.

SUMMARY OF THE INVENTION

The contact lenses and the design methods therefor of the present invention overcome the disadvantages associated with the prior art as briefly described above.

In accordance with one aspect, the present invention is directed to a method for improving ophthalmic lenses for the treatment of presbyopia. The method comprises the steps of creating a base optical design with predetermined features for a lens for treating presbyopia, determining the power profile of the base optical design, $P_{nominal}$, and scaling the radial location of the predetermined features within the base optical design in proportion to the population average pupil size for the degree of ametropia of a target individual.

In accordance with another aspect, the present invention is directed to a method for improving ophthalmic lenses for the treatment of presbyopia. The method comprises the steps of creating a base optical design with predetermined features for a lens for treating presbyopia, determining the power profile of the base optical design, $P_{nominal}$, and scaling the radial location of the predetermined features within the base optical design in proportion to a measured pupil size of an individual.

In accordance with yet another aspect, the present invention is directed to a method for improving ophthalmic lenses for the treatment of presbyopia. The method comprises the steps of creating a base optical design with predetermined features for a lens for treating presbyopia, determining the power profile of the base optical design at a nominal prescription power, creating a visual merit function for optimization, and minimizing the difference between the visual merit function at the nominal prescription power and the visual merit function at the prescription powers other than at the nominal prescription power.

In accordance with still yet another aspect, the present invention is directed to a set of lenses for treating presbyopia over a range of degrees of ametropia. The set of lenses being designed by creating a base optical design with predetermined features for a lens for treating presbyopia, determining the power profile of the base optical design, $P_{nominal}$, and scaling the radial location of the predetermined features within the base optical design in proportion to the population average pupil size for the degree of ametropia of a target individual.

In accordance with another aspect, the present invention is directed to a set of lenses for treating presbyopia over a range of degrees of ametropia. The set of lenses being designed by creating a base optical design with predetermined features for a lens for treating presbyopia, determining the power profile of the base optical design, $P_{nominal}$, and scaling the radial location of the predetermined features within the base optical design in proportion to a measured pupil size of an individual.

In accordance with yet another aspect, the present invention is directed to a set of lenses for treating presbyopia over a range of degrees of ametropia. The set of lenses being designed by creating a base optical design with predetermined features for a lens for treating presbyopia, determining the power profile of the base optical design at a nominal prescription power, creating a visual merit function for optimization, and minimizing the difference between the visual merit function at the nominal prescription power and the visual merit function at the prescription powers other than at the nominal prescription power.

In accordance with still another aspect, the present invention is directed to a set of lenses for treating presbyopia over a range of degrees of ametropia. The set of lenses being designed with a power profile given by $$P_{Rx}(r) = P_2(M_1 * r + M_2 * r^2 + \dots) - SA_{eye} * r^2,$$

where $P_2$ is given by $$P_2(r) = P_1 + Rx,$$

and $$P_1(r) = P_{nominal}(r) - Rx_{nominal} + SA_{eye} * r^2,$$

where $SA_{eye}$ is the spherical aberration, r is the radial distance from the center of the lens, and $P_{nominal}(r)$ is the power profile for the nominal design for the correction of an eye with a spherical refractive need of $Rx_{nominal}$ diopters.

The present invention is directed to lenses, for example, contact lenses and intraocular lenses, for the treatment of presbyopia that are scaled based upon pupil size data to ensure that the design provides the same visual experience independent of the level of ametropia of the patient. The present invention is also directed to methods for adjusting the optical designs for presbyopic lenses to account for changes in pupil size to ensure that the design gives the same visual experience independent of the level of ametropia of the patient. More specifically, the present invention provides a means for adjusting multi-focal and bi-focal designs such that the designs will perform consistently across the population, independent of the degree of ametropia. The optical designs of the lenses for presbyopia described herein are unique for each spherical prescription (Rx) to take into account the fact that the size of the pupil changes with the level or degree of ametropia. The resulting lenses may then be a low and high add, or a low, medium and high add combination, the designs of which may vary by prescription.

While the pupil size data demonstrates that pupil sizes on average are smaller for individuals with hyperopia than for individuals with myopia at and across all light levels, it also shows that there is great variability among subjects for a given level of ametropia. The method of the present invention may also be utilized to scale a design for presbyopia that is constructed and optimized for a particular set of pupil sizes at low, medium and brighter light conditions to be used on an individual that has either a smaller or a larger set of pupil sizes for a given light level. In this case, either the designs are customized for an individual or there may be alternate sets of designs where one of the fit criteria utilized by eye care professionals is patient pupil size, thus providing patients with an improved visual experience.

The first method in accordance with the present invention provides a means to analytically scale a power profile for a design at one prescription to the full range of required prescriptions to provide similar visual performance across the full range of ametropia.

The second method in accordance with the present invention provides a means to scale a power profile for a design at one prescription to the full range of required prescriptions to provide similar visual performance across the full range of ametropia using an optimization method that uses as the merit function a metric that ensures that the visual performance experienced by the wearers depends as little as possible on the level of ametropia.

The overall methodology of the present invention provides a means for modifying existing contact lenses. The methodology allows for creating contact lenses for treating presbyopia with improved visual acuity and a better visual experience for the user.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
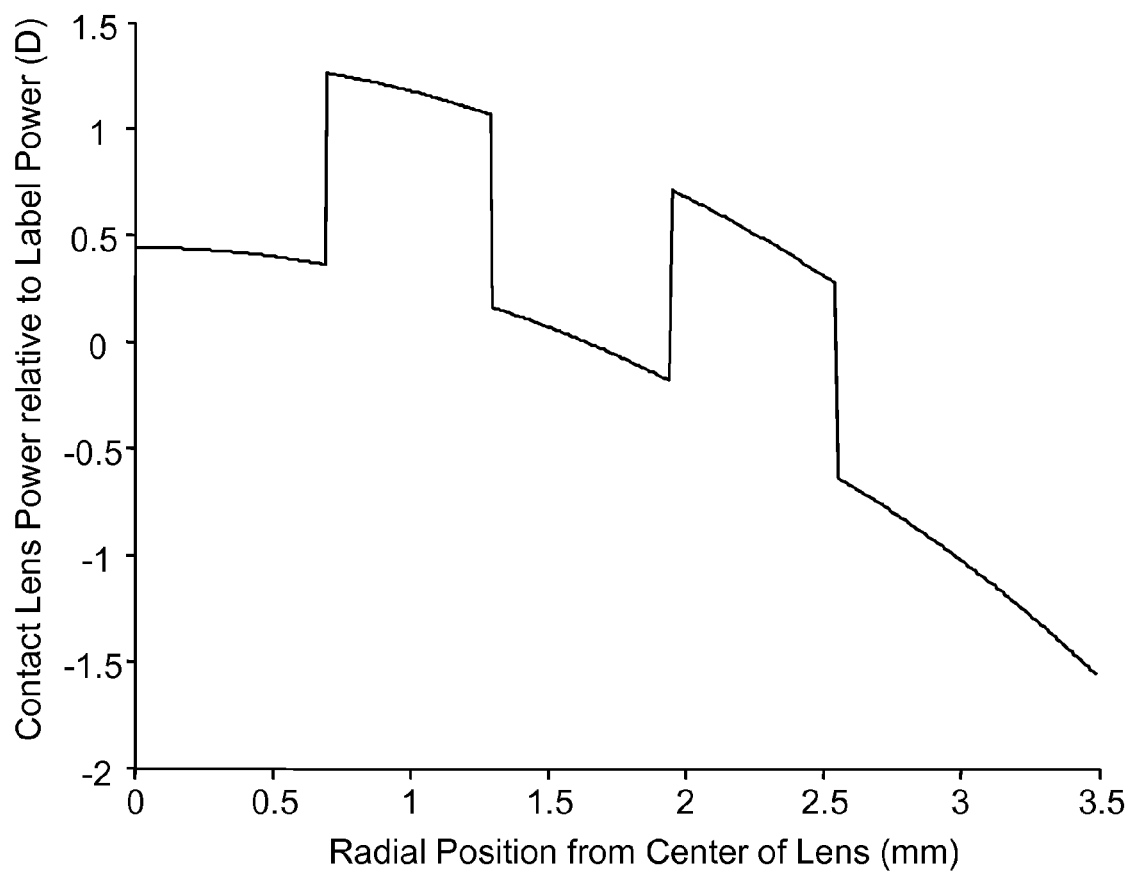
FIG. 1 is a graphical representation of the power profile of an exemplary concentric ring contact lens.
Figure 2:
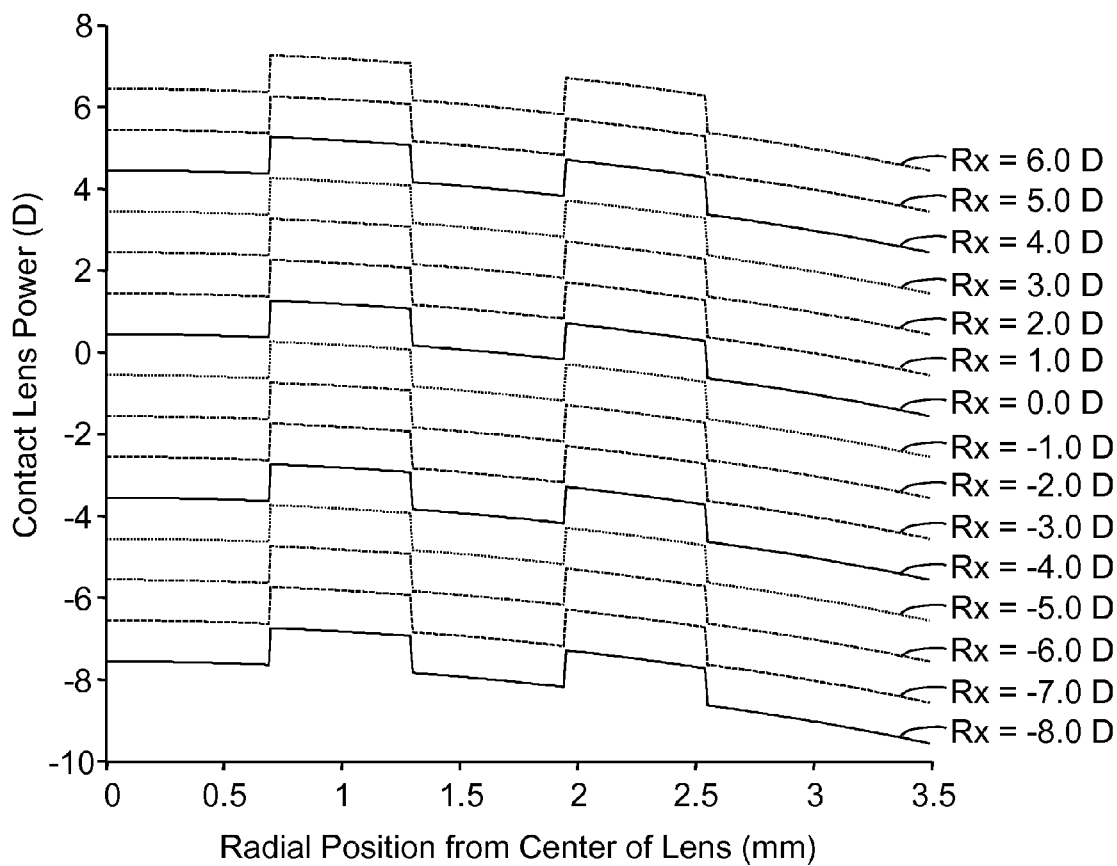
FIG. 2 is a graphical representation of a set of power profiles of an exemplary concentric ring contact lens at different prescription strengths.

The present invention is directed to methods for adjusting the optical designs for lenses for the correction of presbyopia to account for changes in pupil size to ensure that the design gives the same visual experience independent of the level of ametropia of the patient and the resultant lenses. In accordance with one exemplary embodiment, the method provides a means to analytically scale a power profile for a design at one prescription to the full range of required prescriptions to provide similar visual performance across the full range of ametropia. This is the analytical scaling method. In accordance with another exemplary embodiment, the method provides a means to scale a power profile for a design at one prescription to the full range of required prescriptions to provide similar visual performance across the full range of ametropia using an optimization method that utilizes as the merit function or metric that ensures that the visual performance experienced by the users depends as little as possible on the level of ametropia. This is the optimization method. As stated above, the methods may be utilized in any suitable lens, and in the exemplary embodiments described below, a concentric ring design and a progressive multi-faced design are set forth. The processes describe herein utilize the data that indicate pupil sizes for hyperopes and myopes are different as is explained in detail herein.

The present invention may be utilized in a number of ophthalmic lenses, for example, intraocular lenses and contact lenses. For ease of explanation; however, the present invention is described with respect to contact lenses. Contact lenses or contacts are simply lenses placed on the eye. Contact lenses are considered medical devices and may be worn to correct vision and/or for cosmetic or other therapeutic reasons. Contact lenses have been utilized commercially to improve vision since the 1950s. Early contact lenses were made or fabricated from hard materials, were relatively expensive and fragile. In addition, these early contact lenses were fabricated from materials that did not allow sufficient oxygen transmission through the contact lens to the conjunctiva and cornea which potentially could cause a number of adverse clinical effects. Although these contact lenses are still utilized, they are not suitable for all patients due to their poor initial comfort. Later developments in the field gave rise to soft contact lenses, based upon hydrogels, which are extremely popular and widely utilized today. Specifically, silicone hydrogel contact lenses that are available today combine the benefit of silicone, which has extremely high oxygen permeability, with the proven comfort and clinical performance of hydrogels. Essentially, these silicone hydrogel based contact lenses have higher oxygen permeabilities and are generally more comfortable to wear than the contact lenses made of the earlier hard materials. However, these new contact lenses are not totally without limitations.

Currently available contact lenses remain a cost effective means for vision correction. The thin plastic lenses fit over the cornea of the eye to correct vision defects, including myopia or nearsightedness, hyperopia or farsightedness, astigmatism, i.e. asphericity in the cornea, and presbyopia i.e. the loss of the ability of the crystalline lens to accommodate. Contact lenses are available in a variety of forms and are made of a variety of materials to provide different functionality. Daily wear soft contact lenses are typically made from soft polymer-plastic materials combined with water for oxygen permeability. Daily wear soft contact lenses may be daily disposable or extended wear disposable. Daily disposable contact lenses are usually worn for a single day and then thrown away, while extended wear disposable contact lenses are usually worn for a period of up to thirty days. Colored soft contact lenses use different materials to provide different functionality. For example, a visibility tint contact lens uses a light tint to aid the wearer in locating a dropped contact lens, enhancement tint contact lenses have a translucent tint that is meant to enhance one's natural eye color, the color tint contact lens comprises a darker, opaque tint meant to change one's eye color, and the light filtering tint contact lens functions to enhance certain colors while muting others. Rigid gas permeable hard contact lenses are made from silicone polymers but are more rigid than soft contact lenses and thus hold their shape and are more durable. Bifocal contact lenses are designed specifically for patients with presbyopia and are available in both soft and rigid varieties. Toric contact lenses are designed specifically for patients with astigmatism and are also available in both soft and rigid varieties. Combination lenses combining different aspects of the above are also available, for example, hybrid contact lenses.

For purposes of the present invention a contact lens is defined by at least two distinct regions. The inner region or optical zone from which the vision correction is obtained and the outer peripheral zone of the contact lens that provides mechanical stability of the contact lens on eye. In some cases or contact lens designs an intermediate zone or region located between the inner optical zone and the outer peripheral zone may be used for blending the two aforementioned zones in a smooth manner such that discontinuities do not occur. A contact lens is also defined by a front surface or surface power, a back curve or base curve and an edge.

The inner region or optical zone provides vision correction and is designed for a specific need such as single vision myopia or hyperopia correction, astigmatism vision correction, bi-focal vision correction, multi-focal vision correction, custom correction or any other design that may provide vision correction. In other words, the optical zone comprises the visual power correction for the wearer's ametropia and presbyopia. Ametropia is defined as the optical power needed to provide good visual acuity, generally at far distance. It is recognized that this would include myopia or hyperopia, and astigmatism concurrent with either. Presbyopia is corrected by adding algebraically plus optical power to a portion of the optical zone to correct the wearer's near visual acuity requirements. It is recognized that these optical powers may be created by refractive means, diffractive means, or both. The outer periphery or peripheral zone provides stabilization of the contact lens on the eye including centration and orientation. Orientation and stabilization is fundamental when the optical zone includes non-rotationally symmetric features, such as astigmatic correction and/or high order aberrations correction. The intermediate region or zone ensures that the optical zone and the peripheral zone are blended with tangent curves. It is important to note that both the optical zone and the peripheral zone may be designed independently, though sometimes their designs are strongly related when particular requirements are necessary. For example, the design of a toric lens with an astigmatic optical zone might require a particular peripheral zone for maintaining the contact lens at a predetermined orientation on the eye.

Toric contact lenses have different designs than spherical contact lenses. The optical zone portions of toric contact lenses have two powers in them, spherical and cylindrical, created with curvatures generally at right angles to each other. The powers are required to maintain position at the specific angle, cylinder axis, on the eye to provide the required astigmatic vision correction. The mechanical or outer peripheral zone of toric contact lenses typically comprises a stabilization means to properly rotate and orient the cylindrical or astigmatic axis into position while being worn on the eye. Rotating the contact lens to its proper position when the contact lens moves, or when the contact lens is inserted is important in producing a toric contact lens.

The first step in creating lenses in accordance with the present invention is creating an optical design for a bi-focal or multi-focal contact lens. The design types or methods for creating this design are not fixed by or defined by the present invention. Therefore, the design type may be any number of types, including concentric ring designs, designs with continuous power profiles and aspheric surfaces, designs that use diffractive surfaces, and the like. In other words, any suitable lens may be utilized.

The next step in the process is determining the power profile of the design. The power profile, as illustrated in FIG. 1 for an exemplary concentric ring design, is power in diopters calculated as the reciprocal of the distance from the lens in meters to the focal point for light from a given radial position in the pupil. The power $P_{nominal}(r)$ for the nominal design is a function of the radial position r. This lens is designed for an eye with a spherical refractive need, i.e. the spherical prescription, or $Rx_{nominal}$. The notation used here and throughout this description assumes that the power profile is radially symmetric, but this is not a limitation of the present invention. More generally, there is also a polar angle dependence of the power profile.

From the pupil size data provided and described in the figures and specification, it is known that the pupil sizes for hyperopes are smaller than for myopes for equivalent light levels. The central idea of the present invention is to scale the radial location of features within a given design that impact the presbyopic performance so that the location of the features are always located at a constant location relative to the pupil for a given light level. Since the pupil size for a given light level changes in proportion to the degree of ametropia, then it follows that the radial position of the design features must preferably likewise change in proportion to the degree of ametropia.

Starting with the power profile $P_{nominal}(r)$ for the nominal design for the correction of an eye with a spherical refractive need of $Rx_{nominal}$ diopters the power profile $P_1(r)$ is given by $$P_1(r) = P_{nominal}(r) - Rx_{nominal} + SA_{eye} * r^2, \quad (1)$$

where $SA_{eye}$ is the spherical aberration and r is the radial distance from the center of the lens. The power profile $P_1(r)$ is the power profile for the lens plus eye combination for the nominal design placed on an eye with nominal refractive need assuming that the eye has a spherical aberration $SA_{eye}$. The spherical aberration is in units of diopters/mm² and has values typically from 0 to 0.1 D/mm².

The power profile, $P_1(r)$, is next shifted by the power required to make the design suitable for an eye with a refractive need of Rx diopters. This power, $P_2(r)$, is simply given by $$P_2(r) = P_1(r) + Rx. \quad (2)$$

Substituting for $P_1(r)$ from equation (1) into equation (2) results in $$P_2(r) = P_{nominal}(r) + SA_{eye} * r^2 + Rx - Rx_{nominal}. \quad (3)$$

From pupil size data at constant light levels from subjects representing the full range of possible refractive errors one may determine the magnification factor, M, that is applied to the power profile $P_2$ to determine the scaled power profile for the design at a different prescription or Rx. The scaled power $P_{Rx}(r)$ is given by $$P_{Rx}(r) = P_2(M*r) - SA_{eye} * r^2. \quad (4)$$

In accordance with the present invention, the magnification factor M may be approximated by a linear function. The value of M at a given Rx falls within the range of values given by $$M(Rx) = m \cdot (Rx - Rx_{nominal}) + 1 \quad (5)$$

where m varies according to $0.008 < m < 0.012$.

Figure 3:
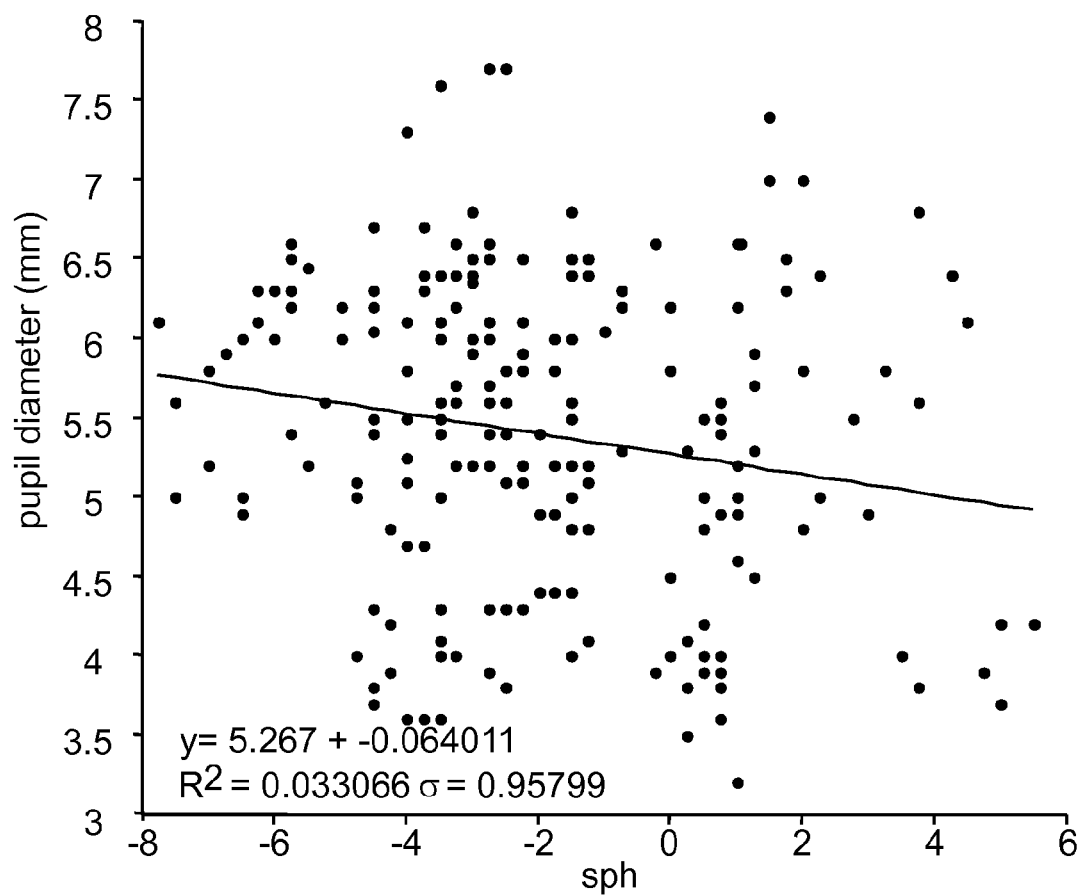
FIG. 3 is a graphical representation of pupil size versus refractive error data at a 2.5 $cd/m^2$ luminance level.
Figure 4:
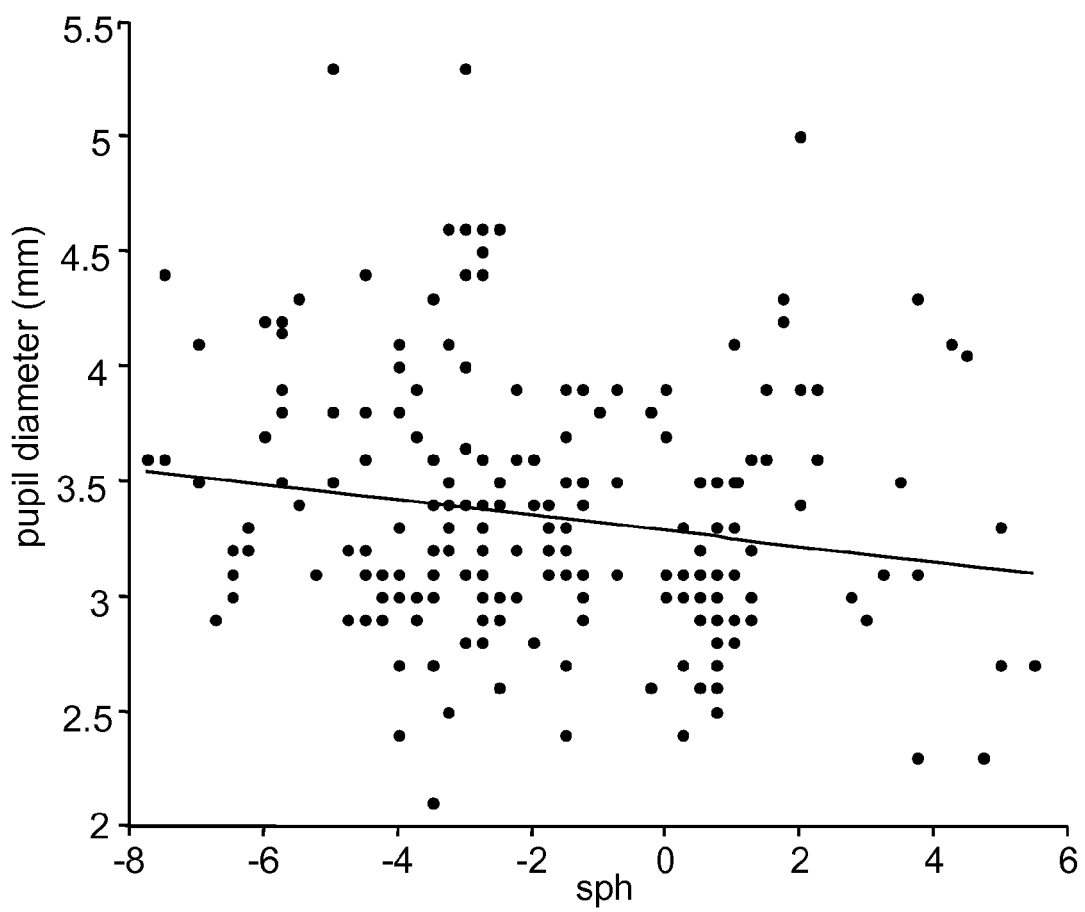
FIG. 4 is a graphical representation of pupil size versus refractive error data at a 50 $cd/m^2$ luminance level.
Figure 5:
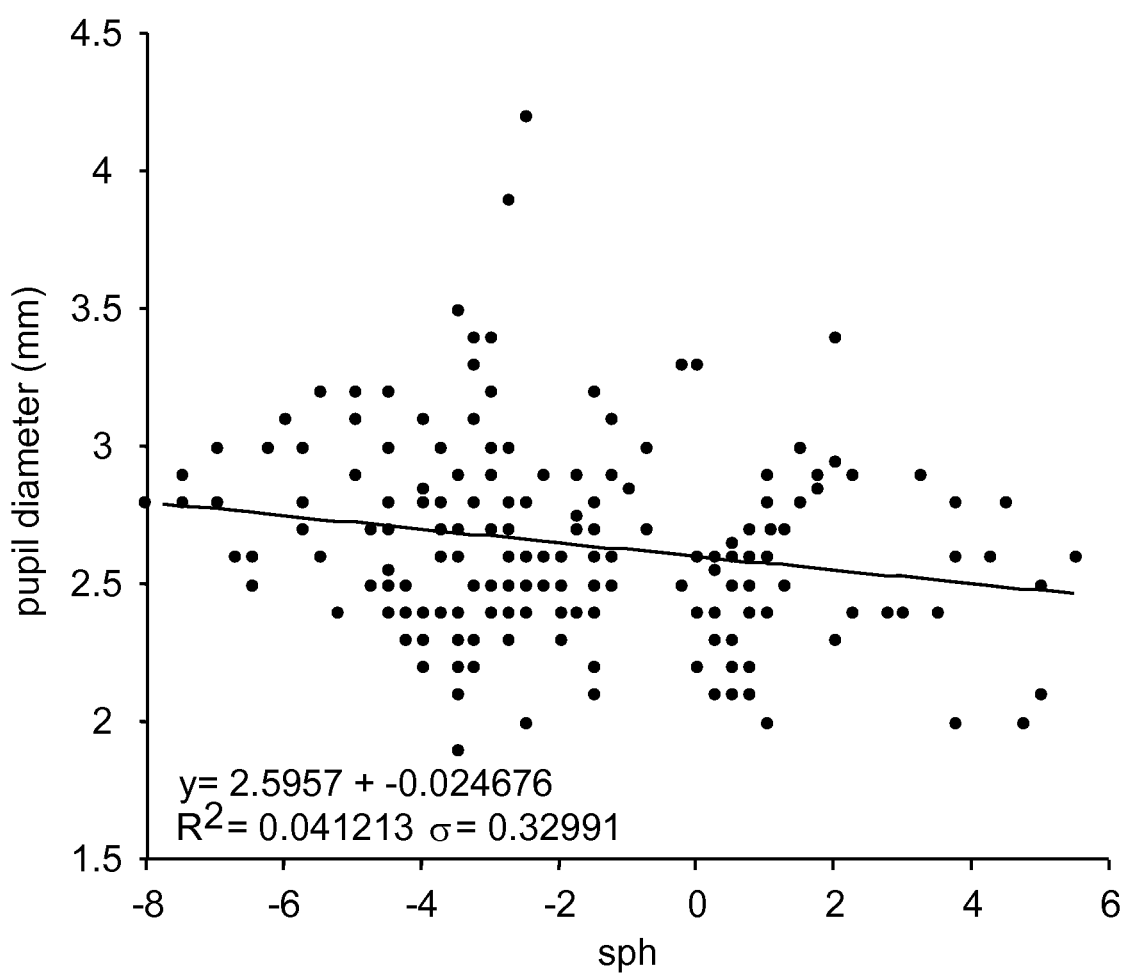
FIG. 5 is a graphical representation of pupil size versus refractive error data at a 250 $cd/m^2$ luminance level.

To better understand this, refer first to the data illustrated in FIGS. 3-5. This data is for subjects greater than forty (40) years old representing the presbyopic population. The pupil diameters were determined for luminance levels of 2.5 cd/m², 50 cd/m², and 250 cd/m². These three fits to the data are plotted together in FIG. 6 as set forth in detail subsequently.

Figure 6:
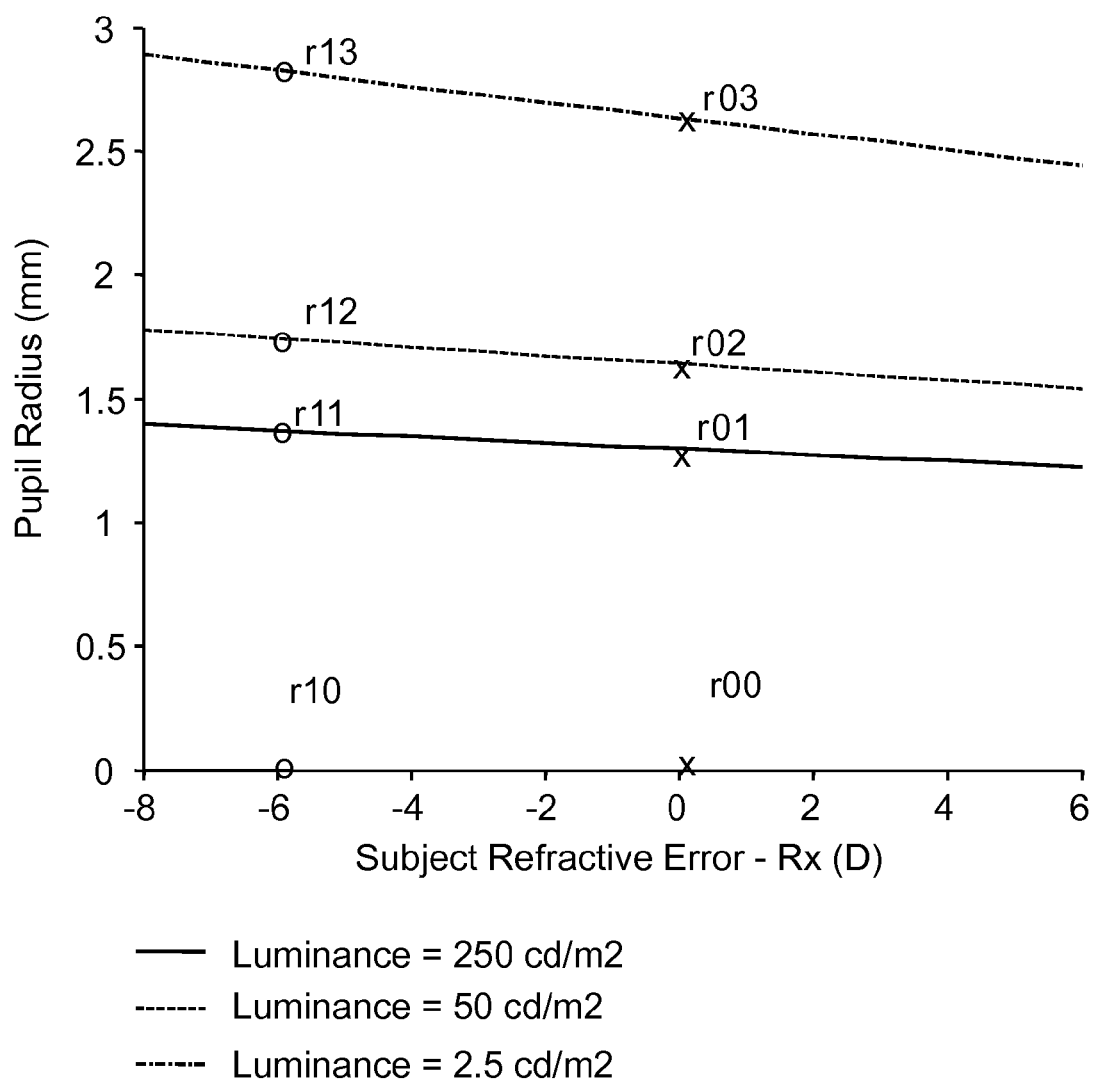
FIG. 6 is a graphical representation of three fits of the data of FIGS. 3, 4 and 5.

The magnification factor, M, is determined from the pupil data as shown in the following examples. In a first example, the lens is a concentric ring type multi-focal lens. The power profile $P_{nominal}(r)$ at $Rx_{nominal} = 0.0$ D is illustrated in FIG. 1. The pupil radius at three distinct luminance levels is summarized by the plot illustrated in FIG. 6. Referring to FIG. 6, at $Rx_{nominal} = 0$ the radius values r01, r02, and r03 for each of the luminance values tested (250 cd/m², 50 cd/m², and 2.5 cd/m²), in addition to the zero value r00 are determined.

These values may be represented by the vector $\vec{r}_0$ given by $$\vec{r}_0 = [r_{00}\, r_{01}\, r_{02}\, r_{003}]. \quad (6)$$

Likewise, the vector $\vec{r}_1$ is determined from the values at the Rx of the target design. In FIG. 6, the target Rx is 6.0 D, and the vector $\vec{r}_1$ is given by $$\vec{r}_0 = [r_{10}\, r_{11}\, r_{12}\, r_{13}]. \quad (7)$$

The magnification factor M relates $\vec{r}_0$ and $\vec{r}_1$ as follows $$\vec{r}_0 = M \cdot \vec{r}_1. \quad (8)$$

M is determined numerically, preferably by a least squares minimization.

Alternately, the factor relating $\vec{r}_0$ and $\vec{r}_1$ may be a higher order function such as a quadratic or cubic function to provide a better fit to the pupil data. In this case equation (4) may become $$P_{Rx}(r) = P_2(M_1 * r + M_2 * r^2 + \ldots) - SA_{eye} * r^2. \quad (9)$$

Figure 7:
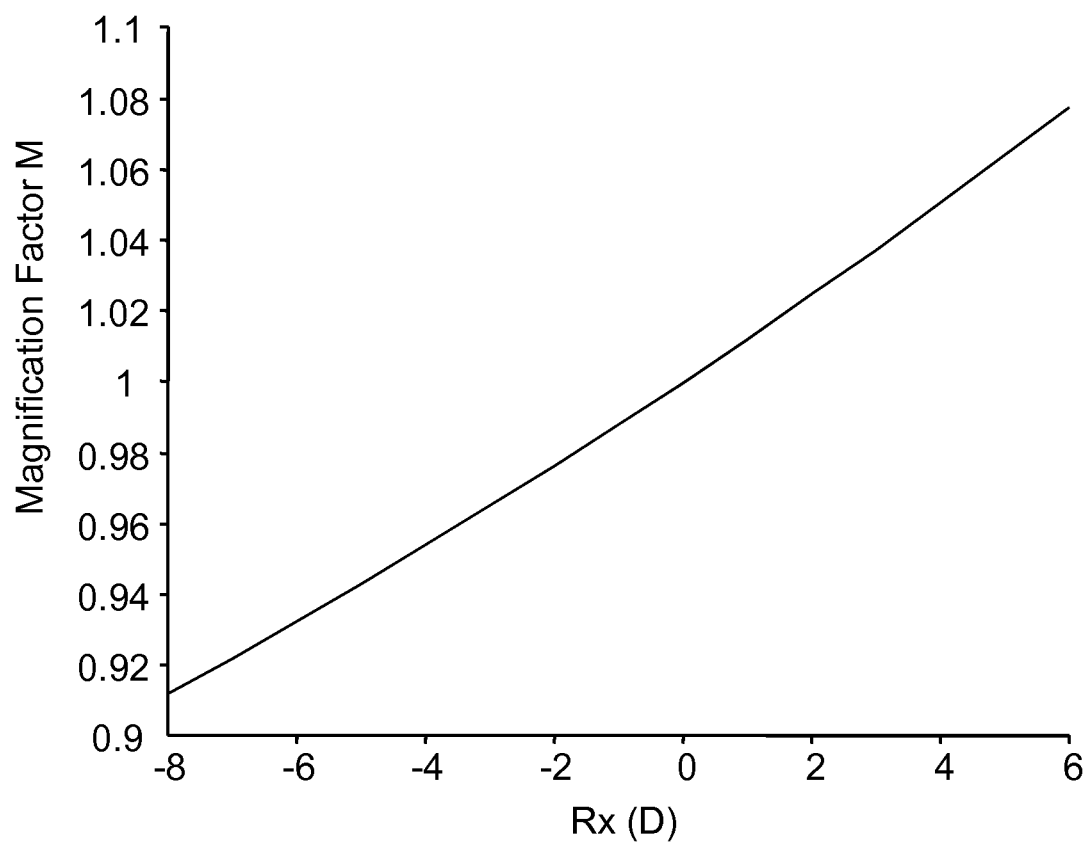
FIG. 7 is a graphical representation of magnification factor as a function of Rx.

FIG. 7 illustrates, for this example, the magnification factors as a function of Rx. Note that M=1 at $Rx_{nominal}$=0, which is as expected.

Figure 8:
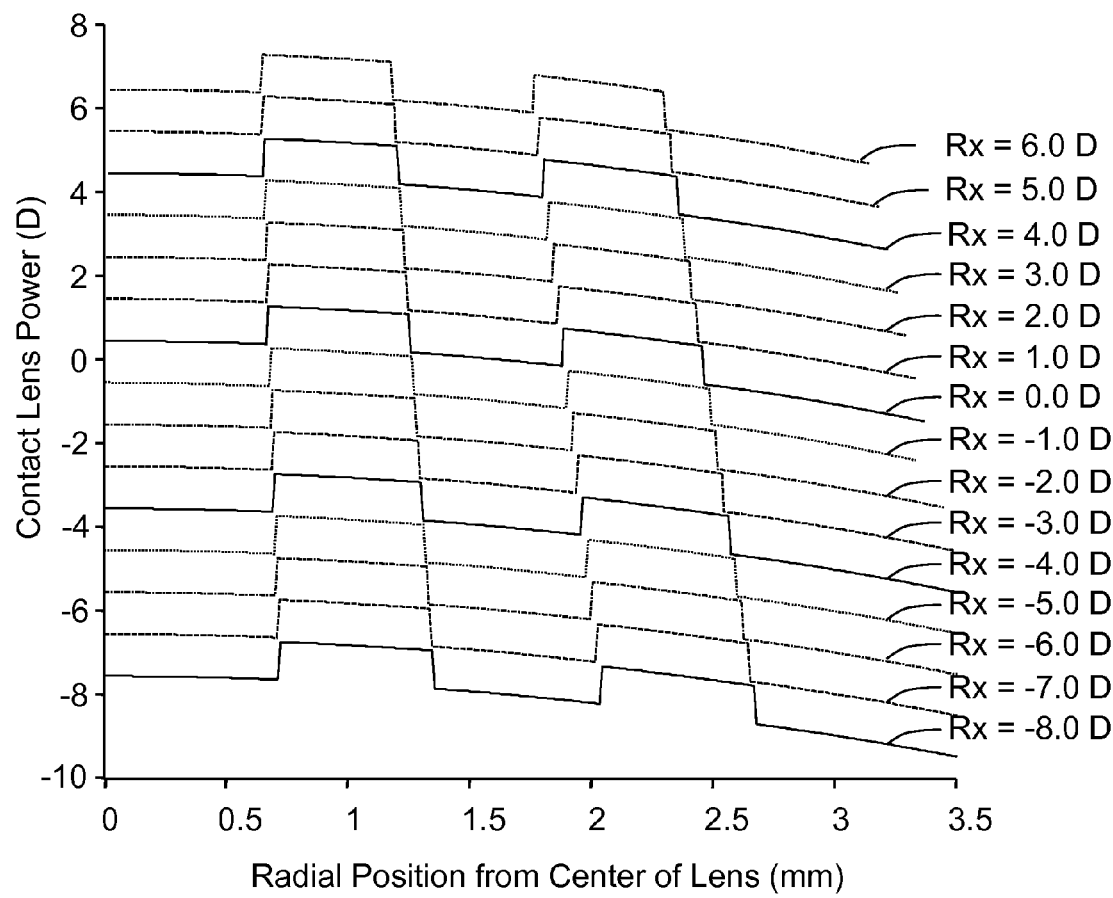
FIG. 8 is a graphical representation of a family of power profiles.
Figure 9A:
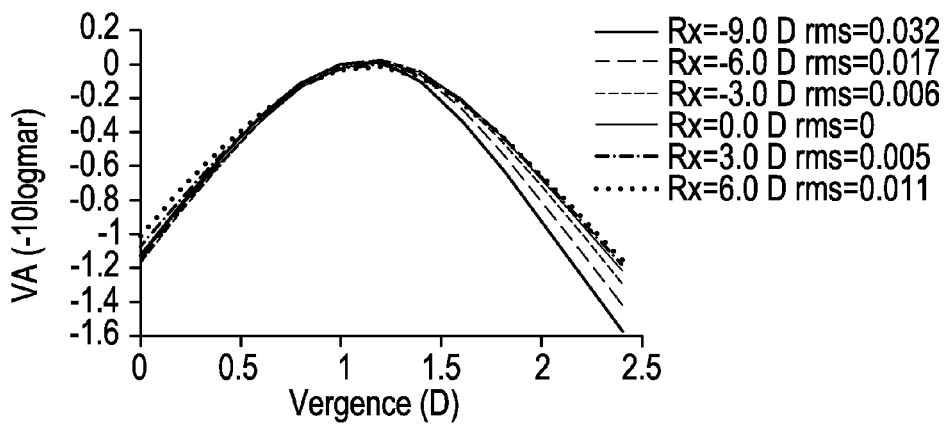
FIG. 9 is a series of graphical representations of predicted logmar acuity versus vergence for three different design methods on a concentric ring lens.
Figure 9B:
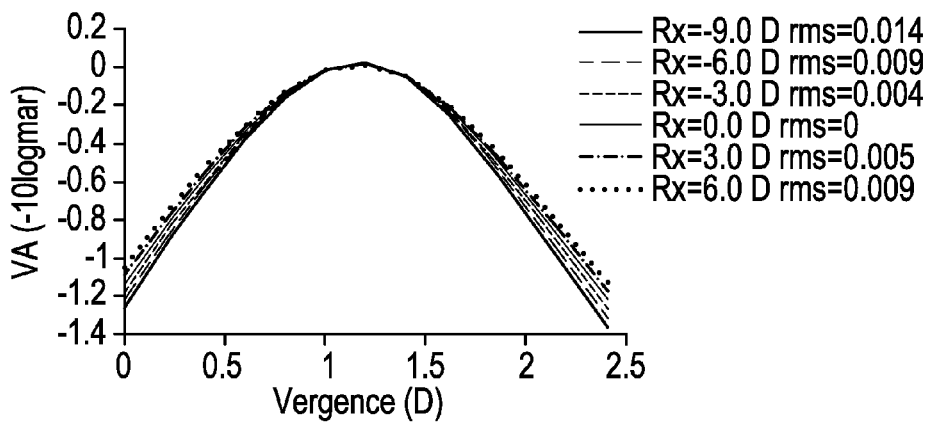
Figure 9C:
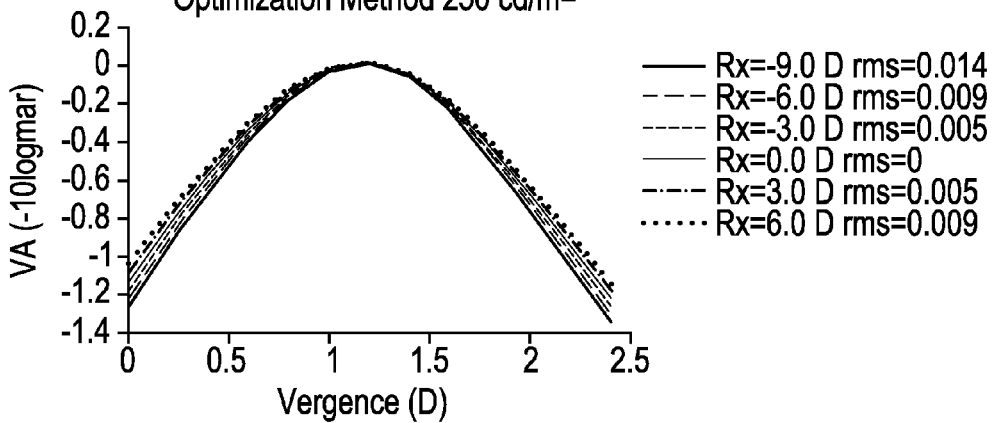
Figure 9D:
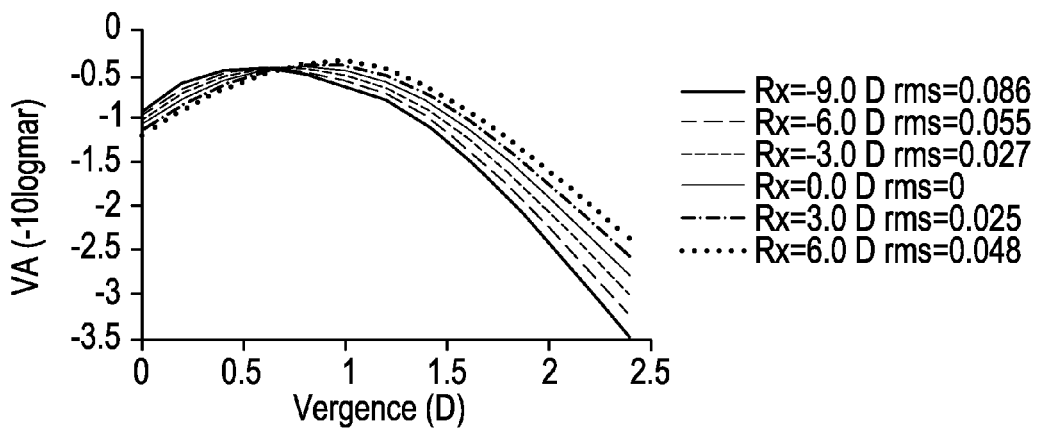
Figure 9E:
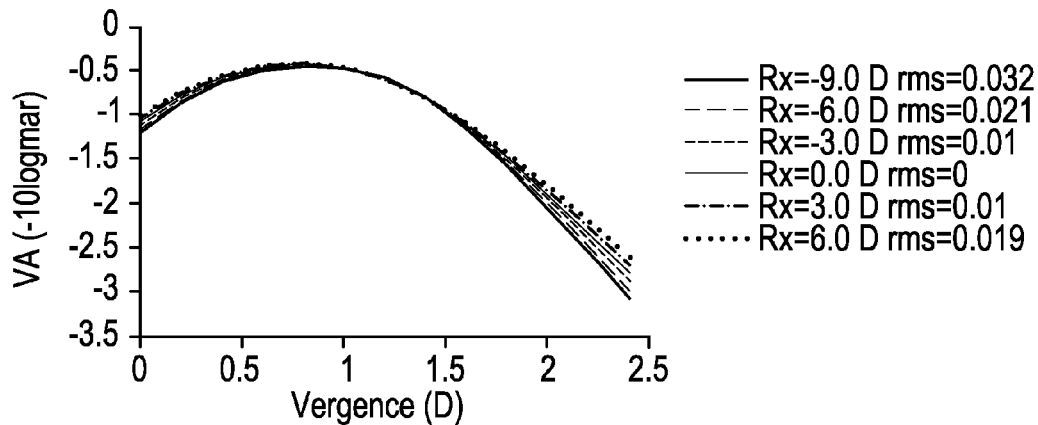
Figure 9F:
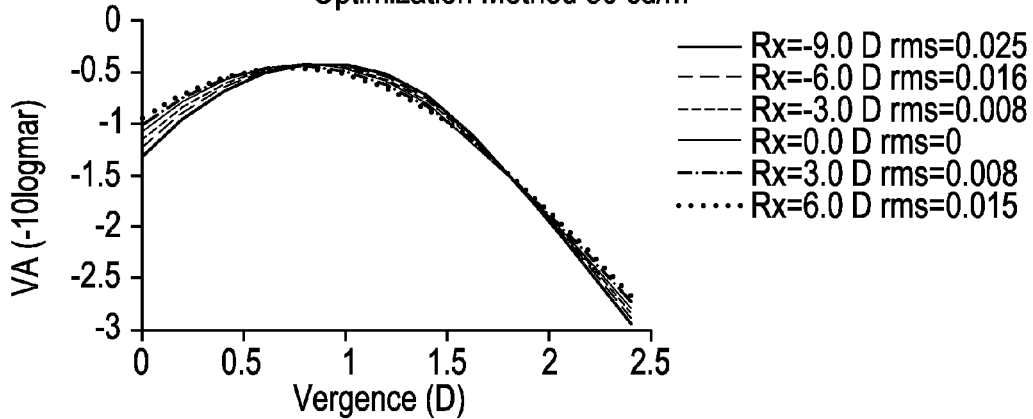
Figure 9G:
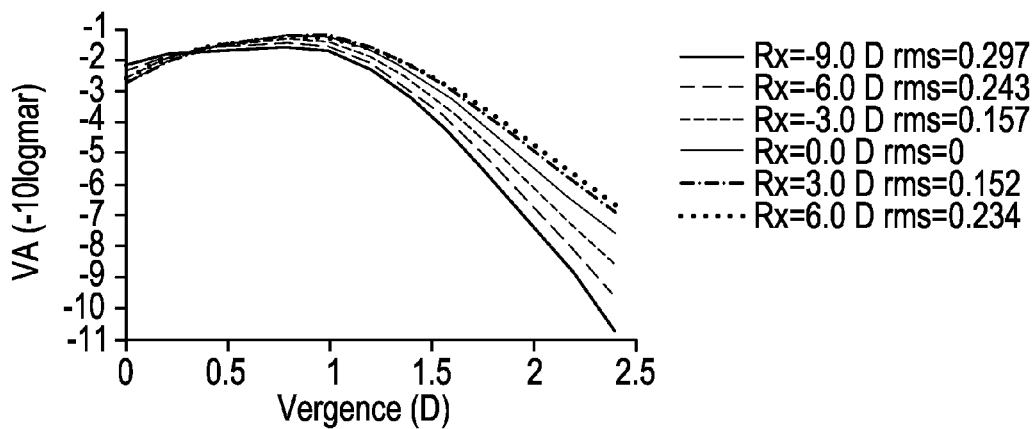
Figure 9H:
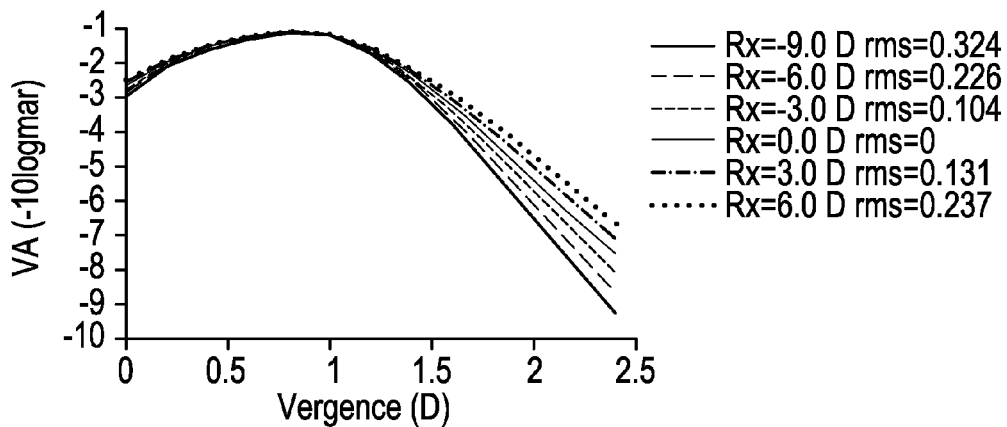
Figure 9I:
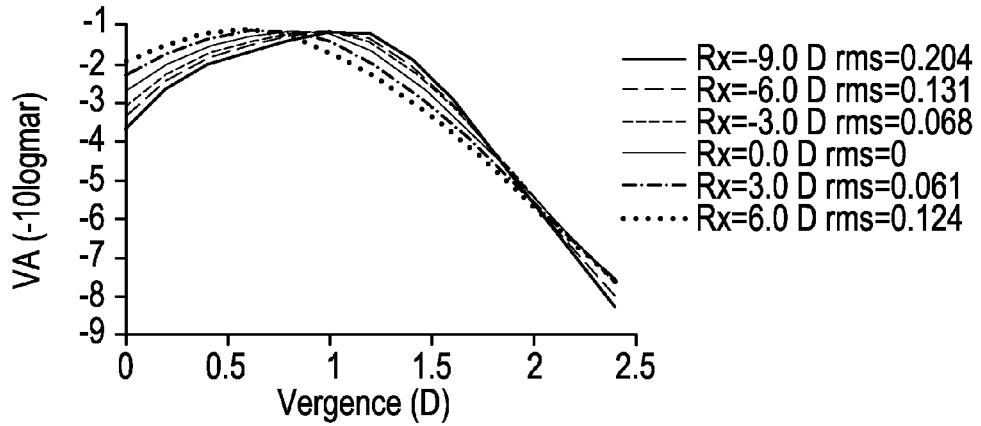
Figure 10C:
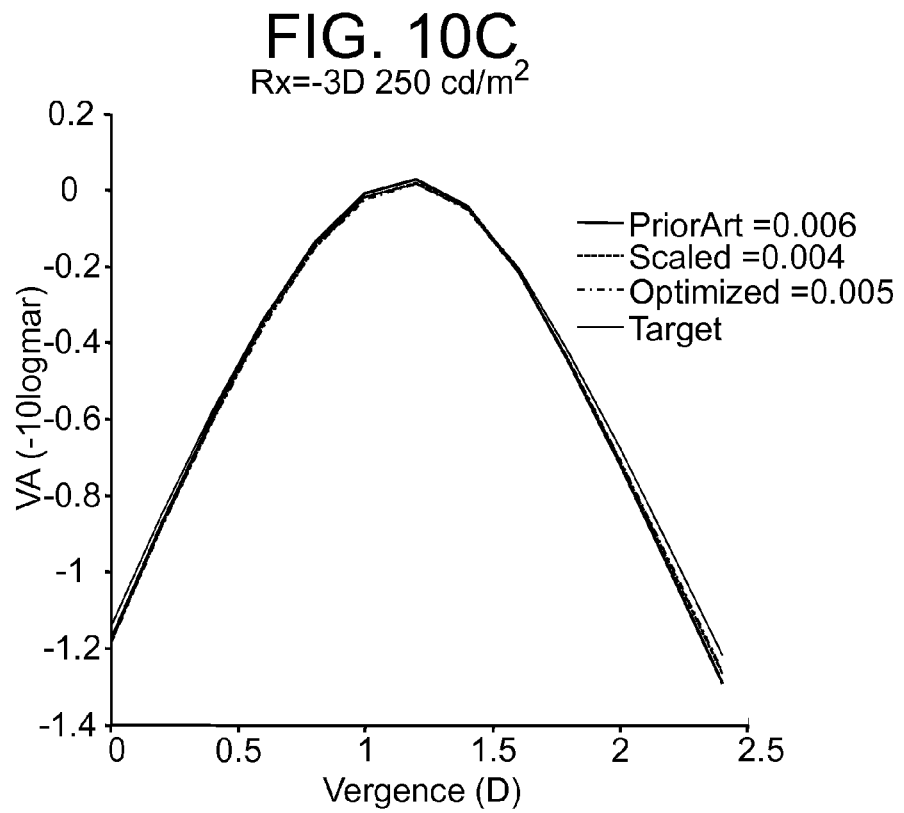
FIGS. 10-12 are simplified replots of the data illustrated in FIG. 9.
Figure 10D:
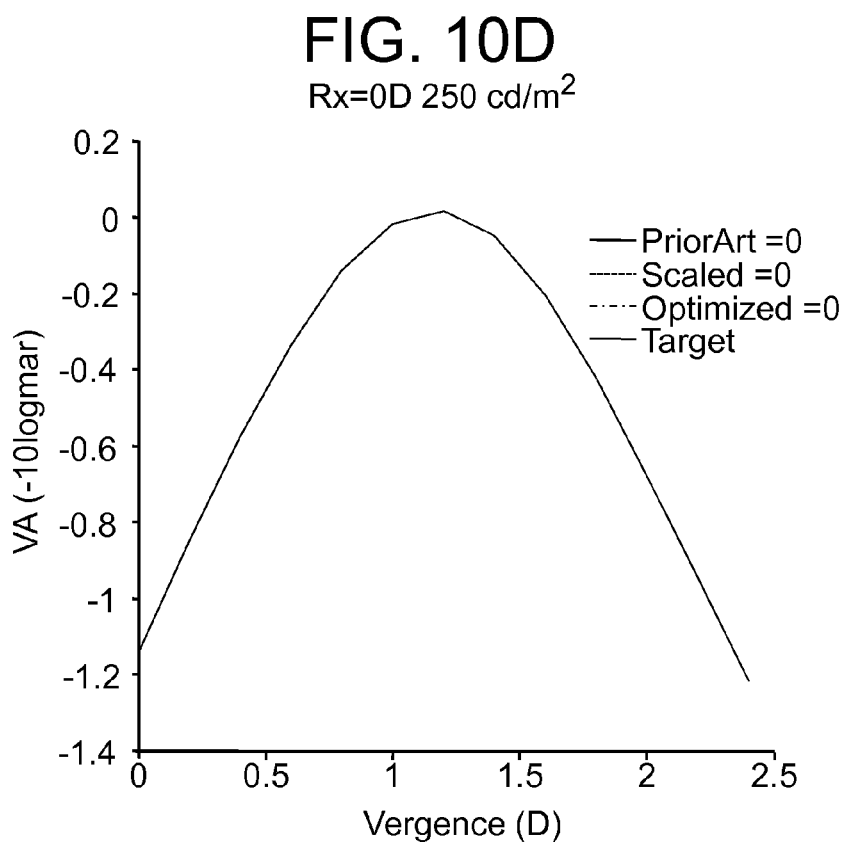
Figure 10E:
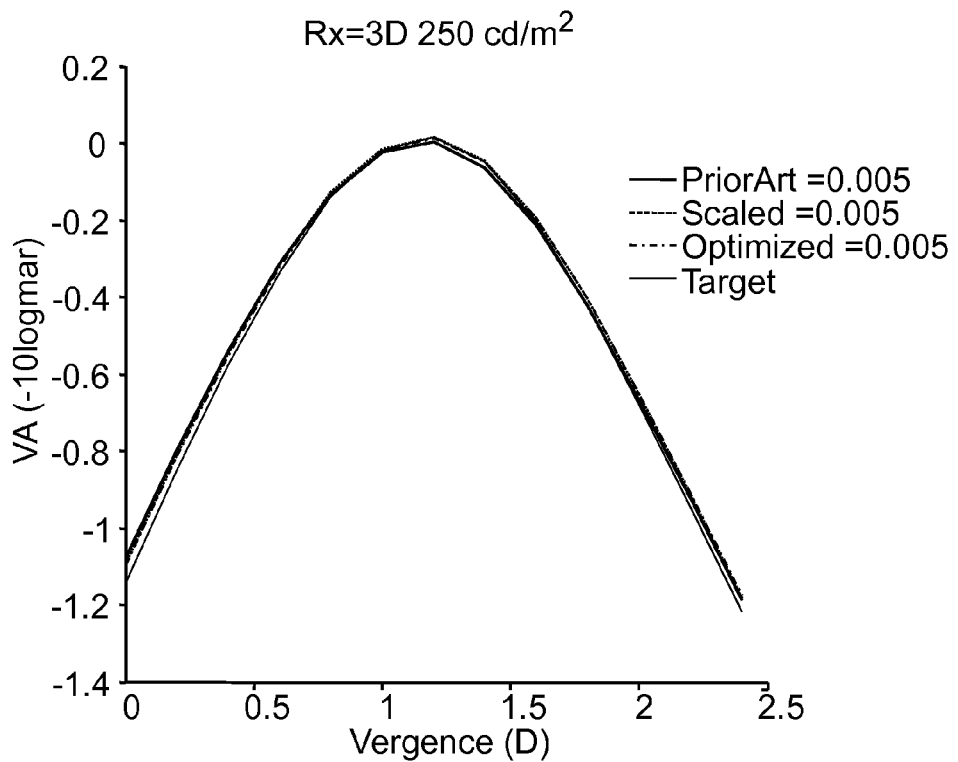
Figure 10F:
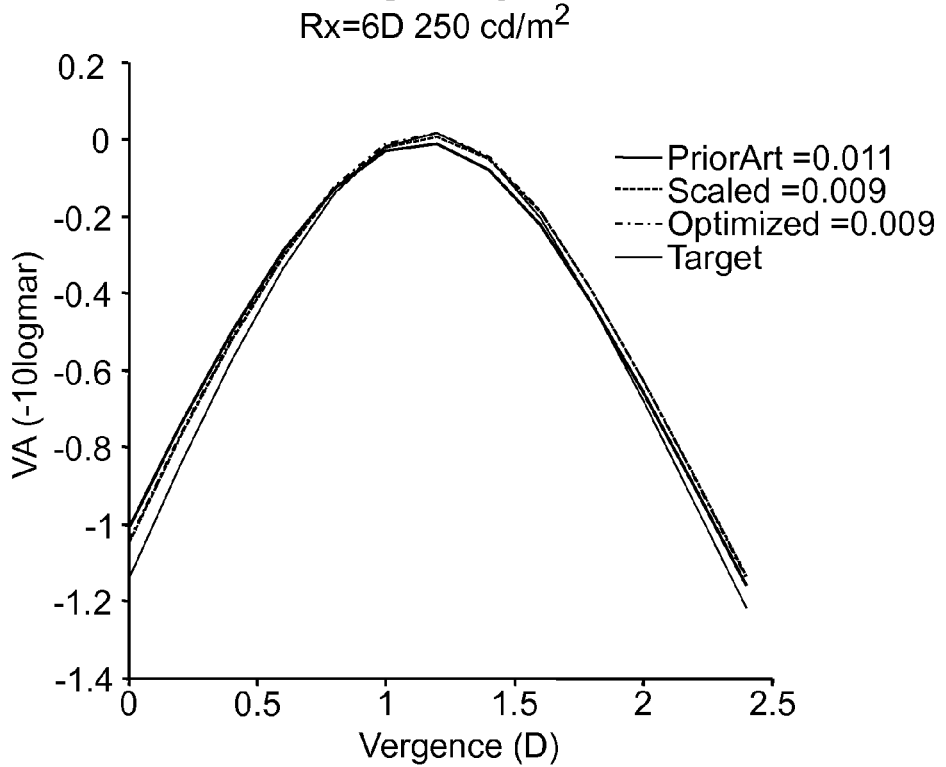

Applying these magnification factors across a range of target Rx values from −8.0 D to +6.0 D in 1.0 D increments results in the family of power profiles illustrated in FIG. 8. For hyperopes, who have smaller pupil sizes, the features in the power profile are located more toward the center of the optics. For myopes, who have larger pupil sizes, the features in the power profile are located more toward the periphery of the optic.

To further refine the mapping to alternate pupil sizes or as an alternate to the calculations set forth above, an optimization procedure may be implemented whereby the power profile at Rx values other than $Rx_{nominal}$ are determined which minimize the difference between a visual performance metric at the alternate Rx's and the visual performance metric at $Rx_{nominal}$. U.S. Pat. No. 7,625,086 describes a method for calculating a predicted logmar acuity ("VA") for a contact lens and eye combination. This VA calculation may be used as a visual performance metric for optimization, although other metrics such as modulated transfer function (MTF) or root mean square (RMS) spot size are also possible. The preferred method for creating the merit function is to calculate the through vergence (object distance from infinity to 40 cm, or equivalently in diopters from 0 D to 2.5 D) at $Rx_{nominal}$ for low, medium and high luminance levels and define the merit function as the difference between those VA values and the values at the new Rx (which has different pupil sizes at the designated luminance levels). The power profile of the design is then optimized in a least squares sense to minimize the difference in the through vergence VA between the designs and Rx and $Rx_{nominal}$.

FIG. 9 graphically illustrates, for a concentric ring zone design lens (example 1) a comparison between prior art lenses, lenses made via the scaling method and lenses made via the optimization method. The data is also presented in Table 1 given below. FIG. 9 illustrates three rows and three columns of through vergence calculations for designs from −9 D to +6 D (−9 D, −6 D, −3 D, 0 D, 3 D, and 6 D). In these designs $Rx_{nominal}$=0. The first row is for luminance of 250 cd/m², the second row with 50 cd/m2 and the third row with 2.5 cd/m². The first column illustrates the through vergence results with the power profiles scaled across Rx using the method of the prior art. The middle column illustrates the scaling method and the right column shows the optimization method. On each plot is also shown the RMS value, which is the RMS error between the target through vergence VA at $Rx_{nominal}$ and the actual value. As one can see, in a majority of the cases, the scaling method provides an improvement over the prior art and the optimization method provides an even further improvement consistently resulting in lower RMS values for the three pupil sizes for all Rx's.

Figure 11A:
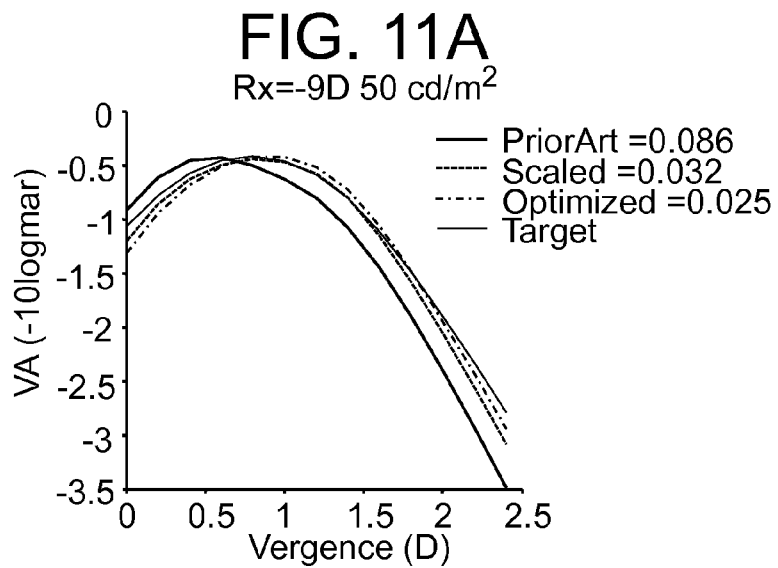
Figure 11B:
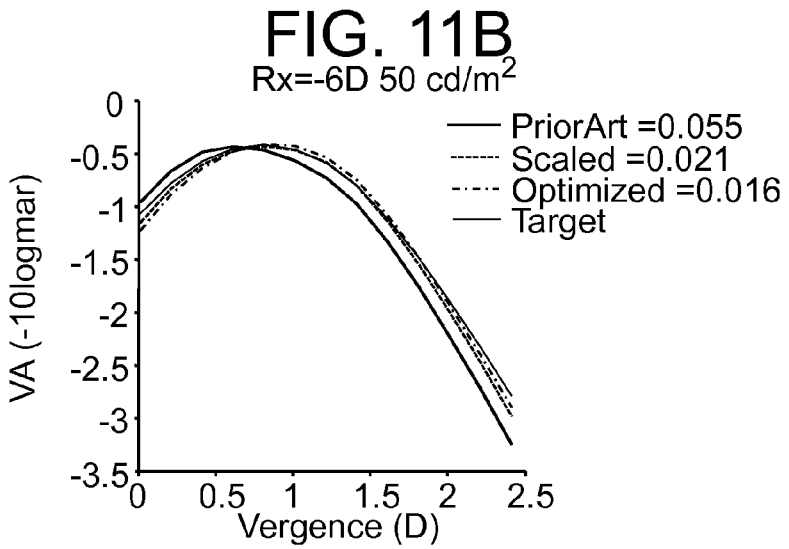
Figure 11C:
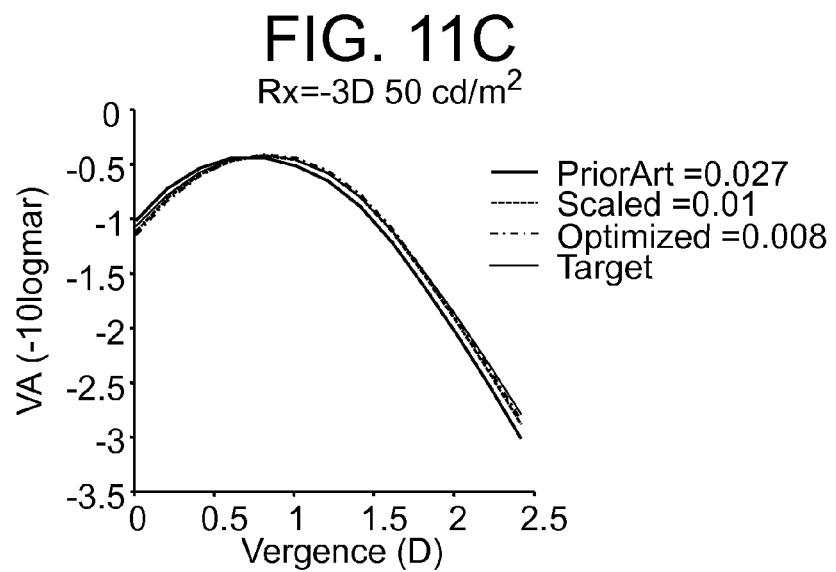
Figure 12D:
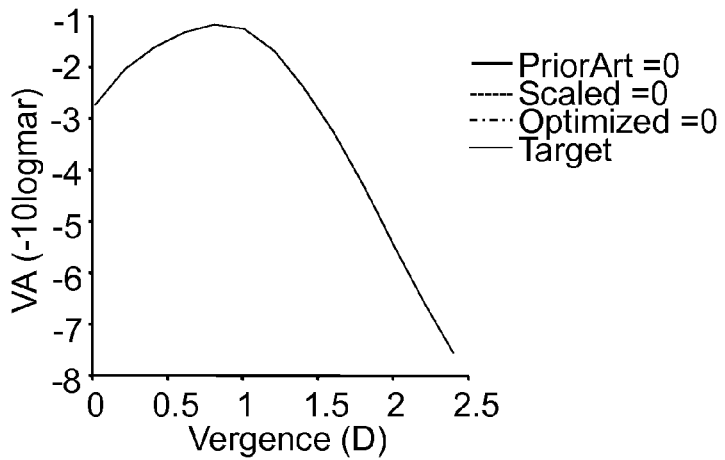
Figure 12E:
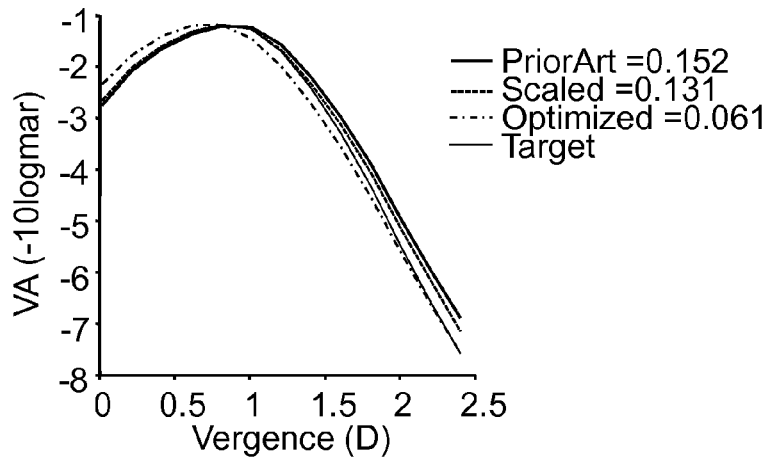
Figure 12F:
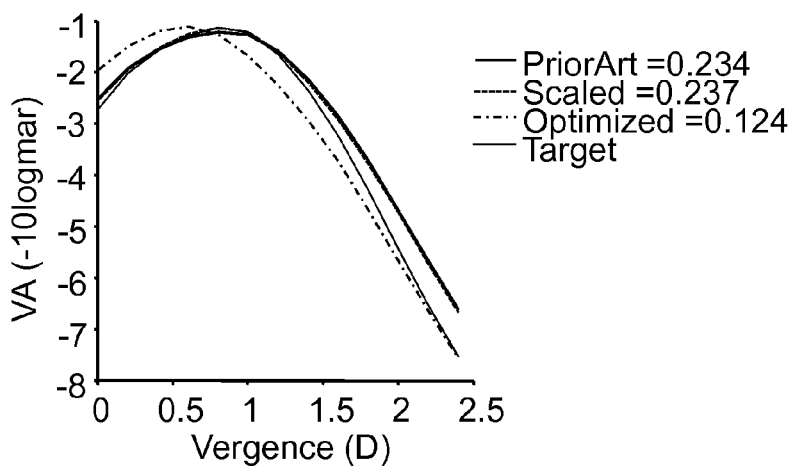

FIGS. 10-12 are graphical representations of the same data plotted differently and with fewer plots combined so that it is easier to see the advantages of the exemplary methods of the present invention. FIG. 10 is for 250 cd/m2, FIG. 11 is for 50 cd/m2 and FIG. 12 is for 5 cd/m2.

Figure 13:
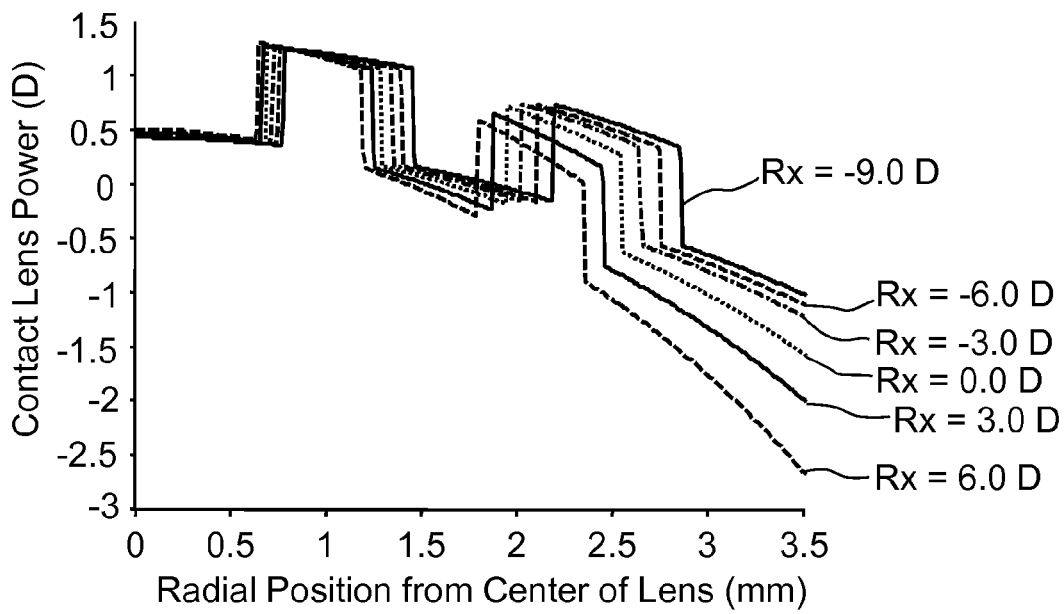
FIG. 13 is a graphical representation of a series of power profiles versus radial position from lens center generated utilizing a scaling method on a concentric ring lens in accordance with the present invention.
Figure 14:
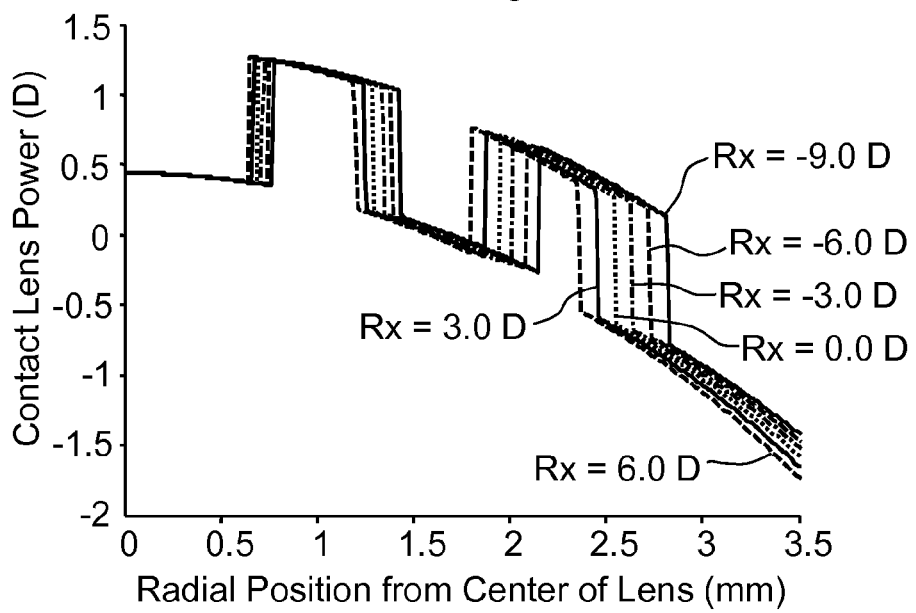
FIG. 14 is a graphical representation of a series of power profiles versus radial position from lens center generated utilizing an optimization method on a concentric ring lens in accordance with the present invention.

FIG. 14, like FIG. 8, illustrates the power profiles for the resultant designs using the scaling method. In this case, they are all normalized to the same Rx (e.g. Rx=0). FIG. 13 illustrates the power profiles using the optimization method.

TABLE 1

|  | Pupil | Prior | Scaled | Optimized |
| --- | --- | --- | --- | --- |
| Rx = −9 D |  |  |  |  |
| EPD | 2.8 | 0.032 | 0.014 | 0.014 |
| EPD | 3.6 | 0.086 | 0.032 | 0.025 |
| EPD | 5.8 | 0.297 | 0.324 | 0.204 |
| Rx = −6 D |  |  |  |  |
| EPD | 2.7 | 0.017 | 0.009 | 0.009 |
| EPD | 3.5 | 0.055 | 0.021 | 0.016 |
| EPD | 5.7 | 0.243 | 0.226 | 0.131 |
| Rx = −3 D |  |  |  |  |
| EPD | 2.7 | 0.006 | 0.004 | 0.005 |
| EPD | 3.4 | 0.027 | 0.010 | 0.008 |
| EPD | 5.5 | 0.157 | 0.104 | 0.068 |
| Rx-0 D |  |  |  |  |
| EPD | 2.6 | 0.000 | 0.000 | 0.000 |
| EPD | 3.3 | 0.000 | 0.000 | 0.000 |
| EPD | 5.3 | 0.000 | 0.000 | 0.000 |
| Rx = 3 D |  |  |  |  |
| EPD | 2.5 | 0.005 | 0.005 | 0.005 |
| EPD | 3.2 | 0.025 | 0.010 | 0.008 |
| EPD | 5.1 | 0.152 | 0.131 | 0.061 |
| Rx = 6 D |  |  |  |  |
| EPD | 2.4 | 0.011 | 0.009 | 0.009 |
| EPD | 3.1 | 0.048 | 0.019 | 0.015 |
| EPD | 4.9 | 0.234 | 0.237 | 0.124 |

Figure 15:
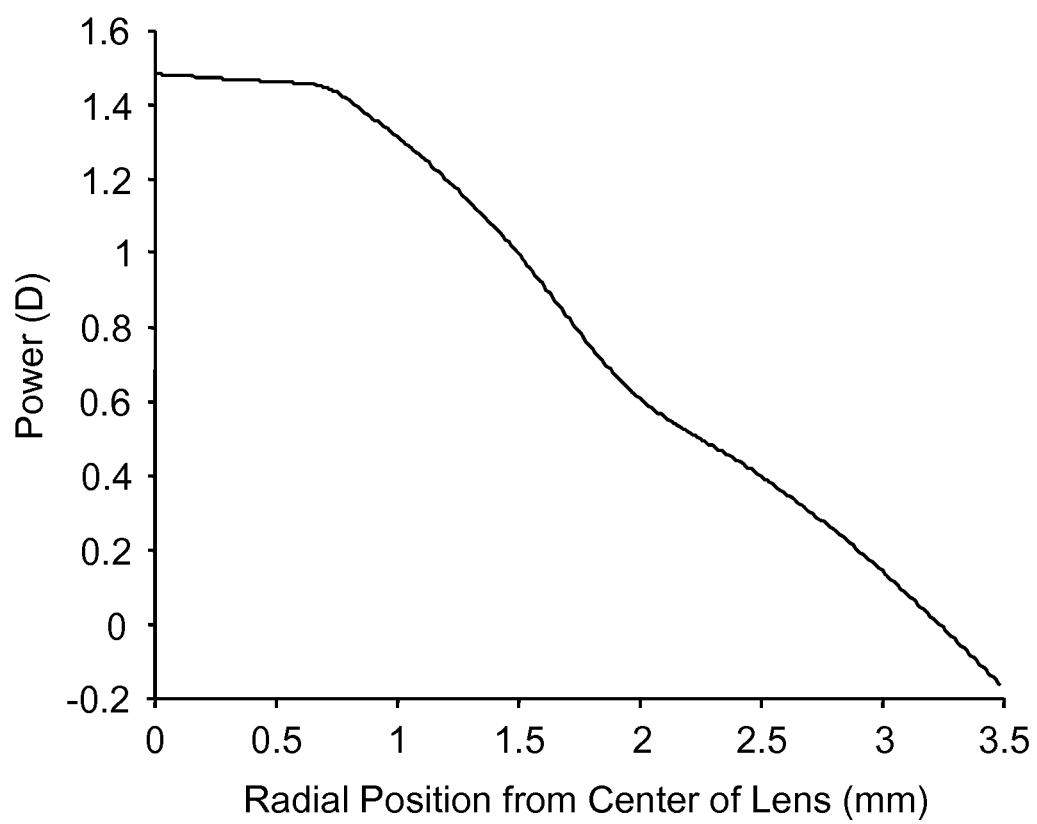
FIG. 15 is a graphical representation of the power profile of an exemplary progressive multi-focal contact lens.
Figure 16:
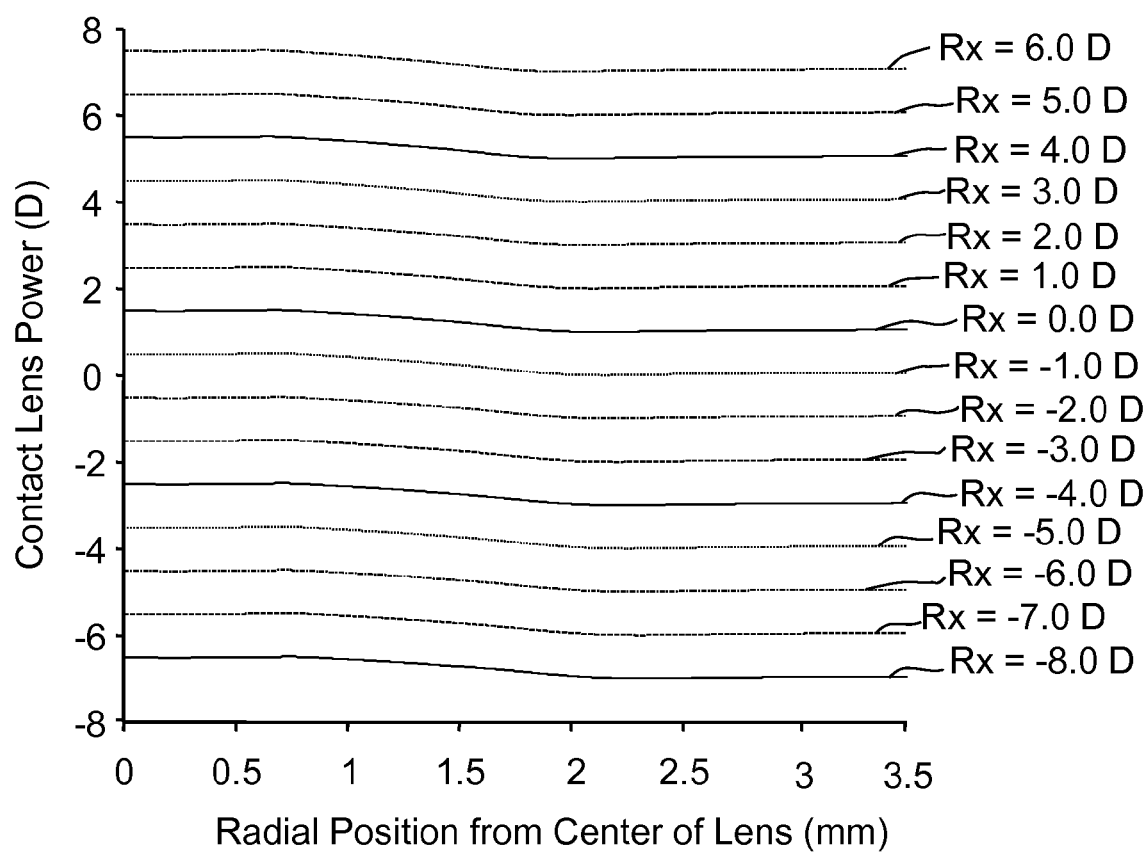
FIG. 16 is a graphical representation of a series of power profiles versus radial position from lens center generated utilizing a scaling method on a progressive multi-focal lens in accordance with the present invention.
Figure 17:
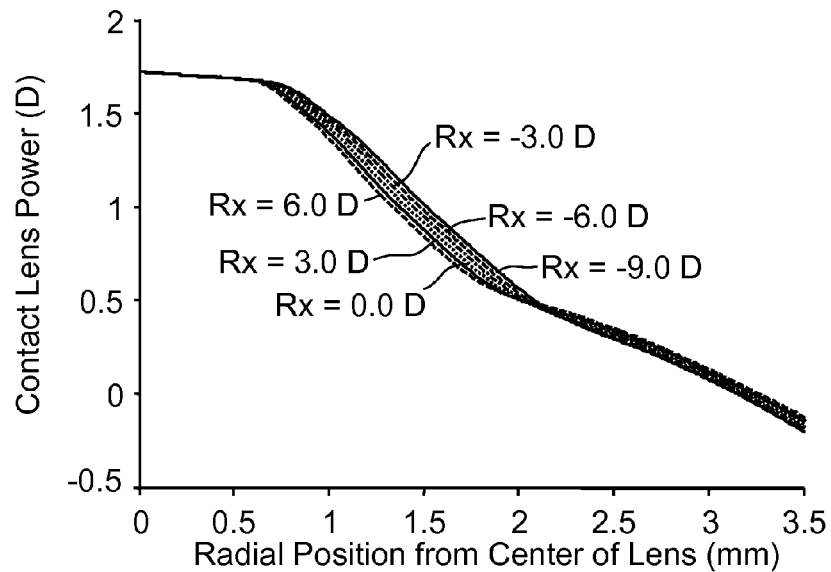
FIG. 17 is a graphical representation of a series of power profiles versus radial position from lens center generated utilizing a scaling method on a progressive multi-focal lens with the Rx subtracted from each in accordance with the present invention.
Figure 18:
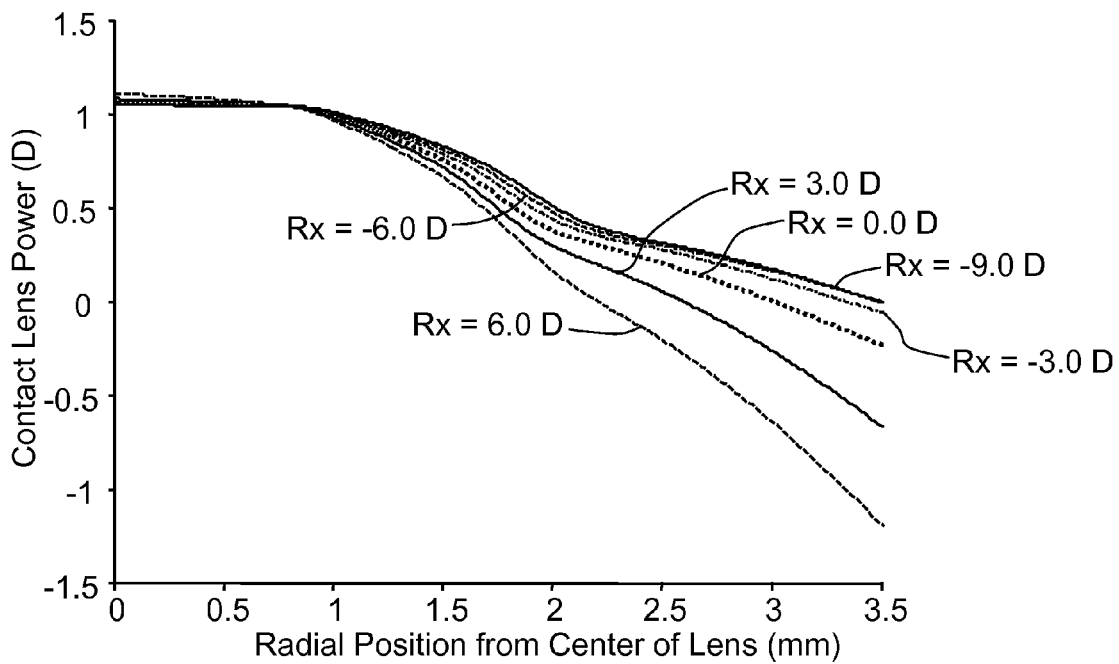
FIG. 18 is a graphical representation of a series of power profiles versus radial position from lens center generated utilizing an optimization method on a progressive multi-focal lens in accordance with the present invention.
Figure 19A:
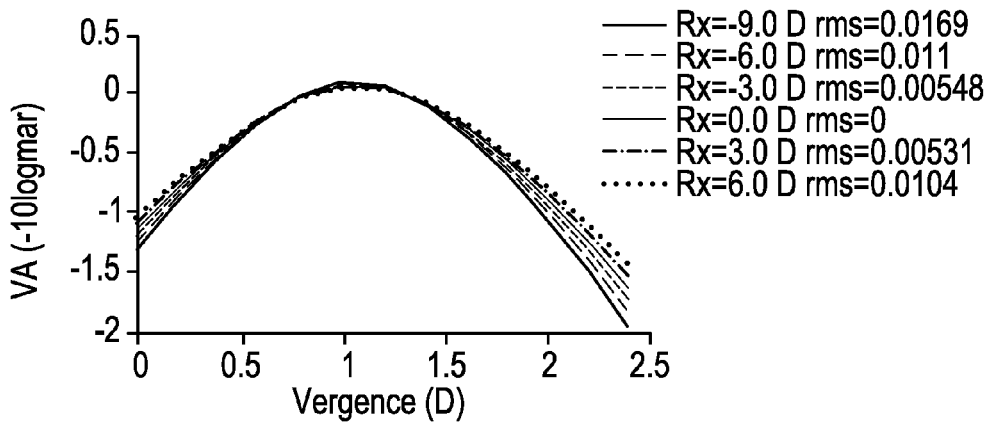
FIG. 19 is a series of graphical representations of predicted longmar acuity versus vergence for three different design methods on a progressive multi-focal lens.
Figure 19B:
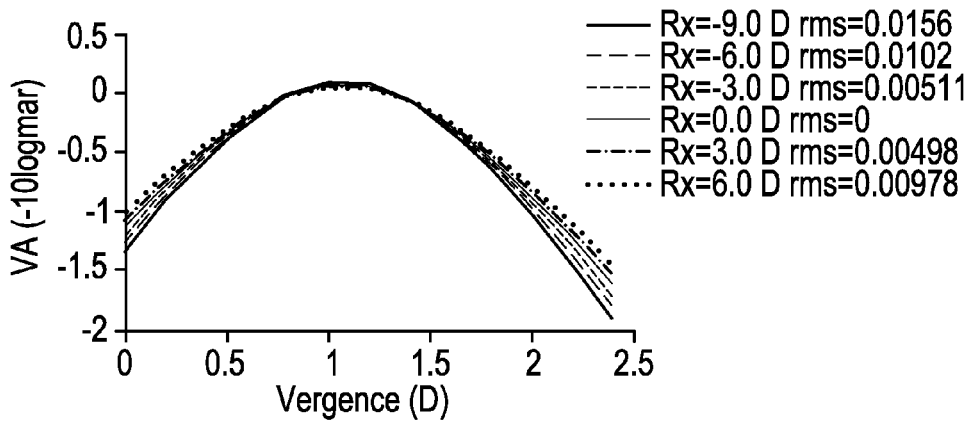
Figure 19C:
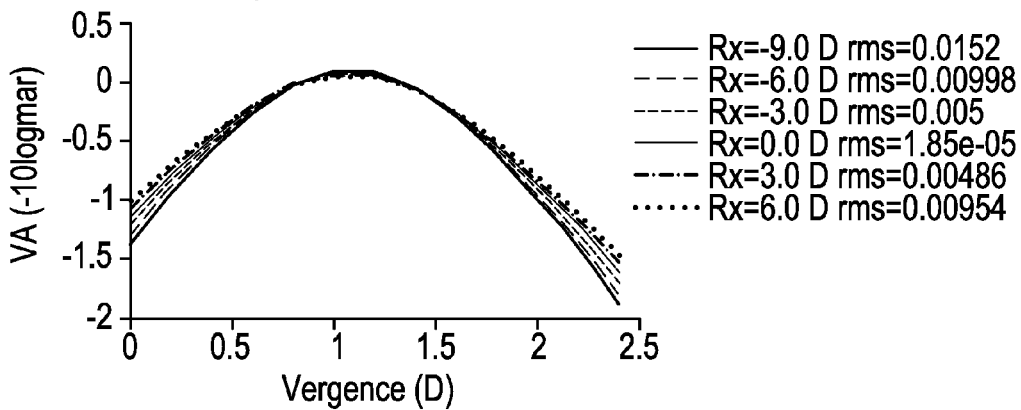
Figure 19D:
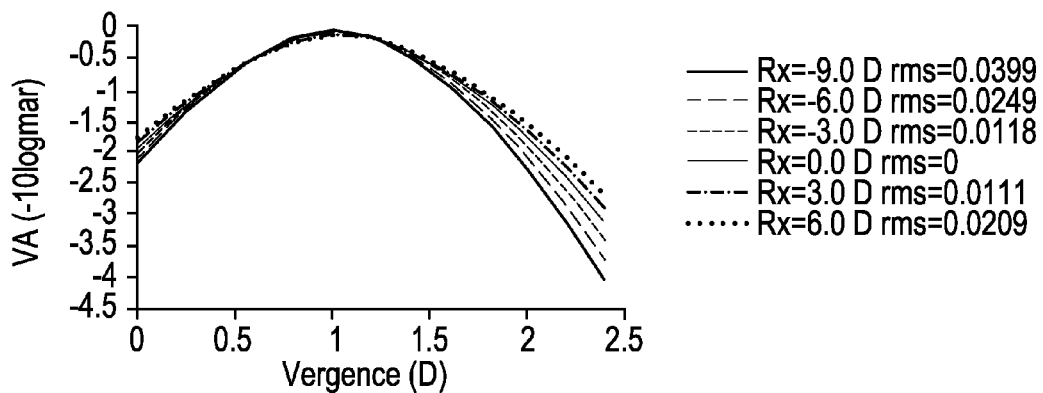
Figure 19E:
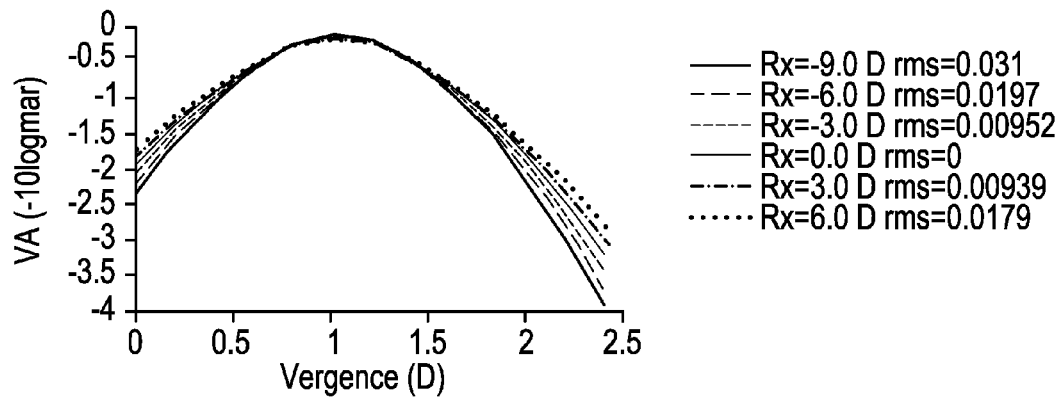
Figure 19F:
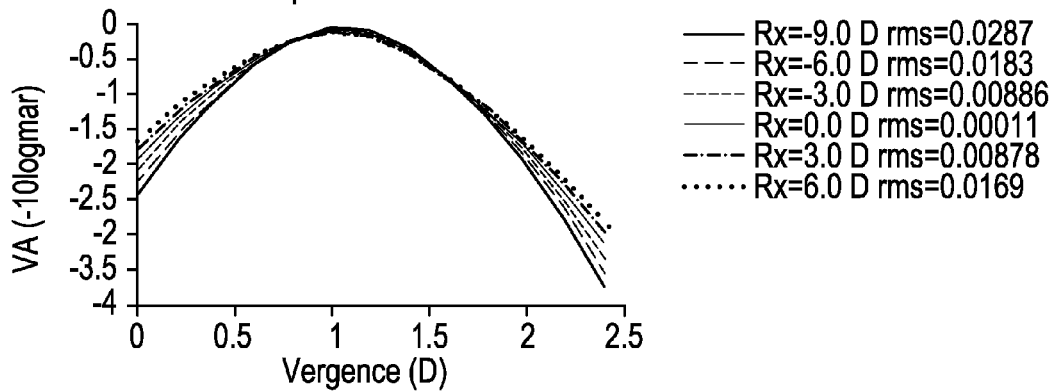
Figure 19G:
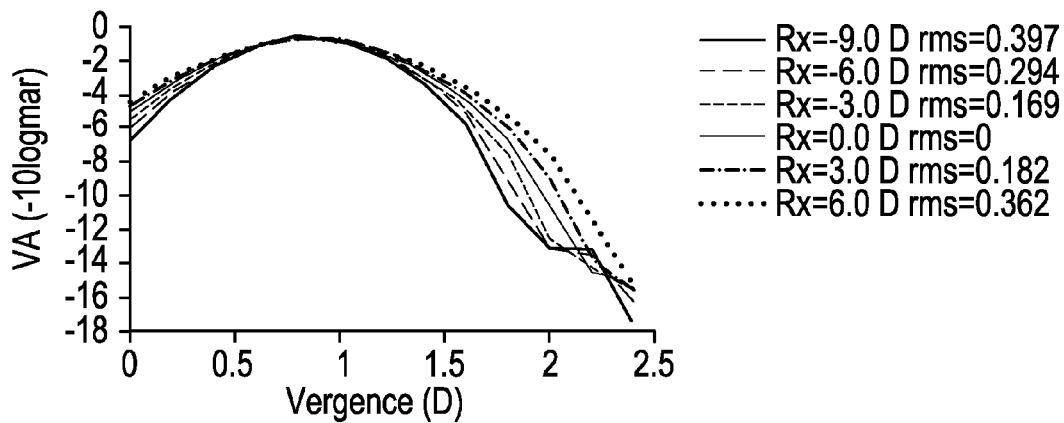
Figure 19H:
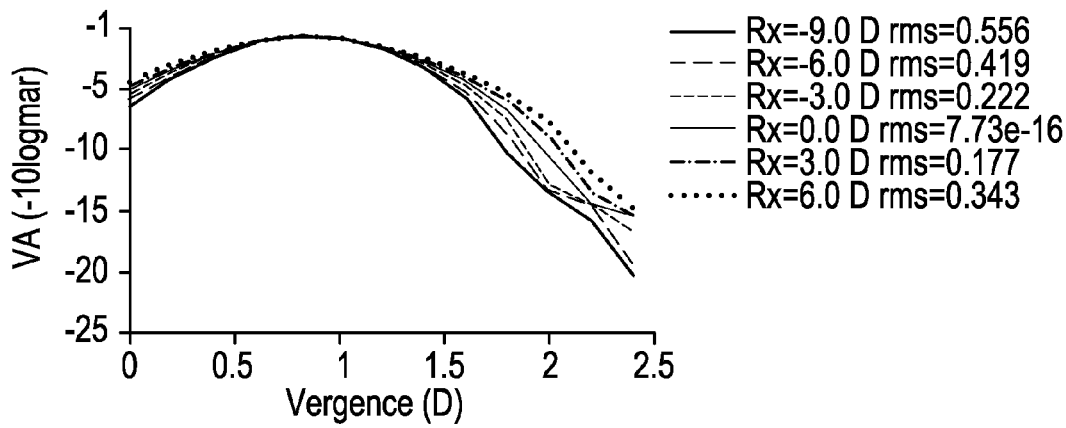
Figure 19I:
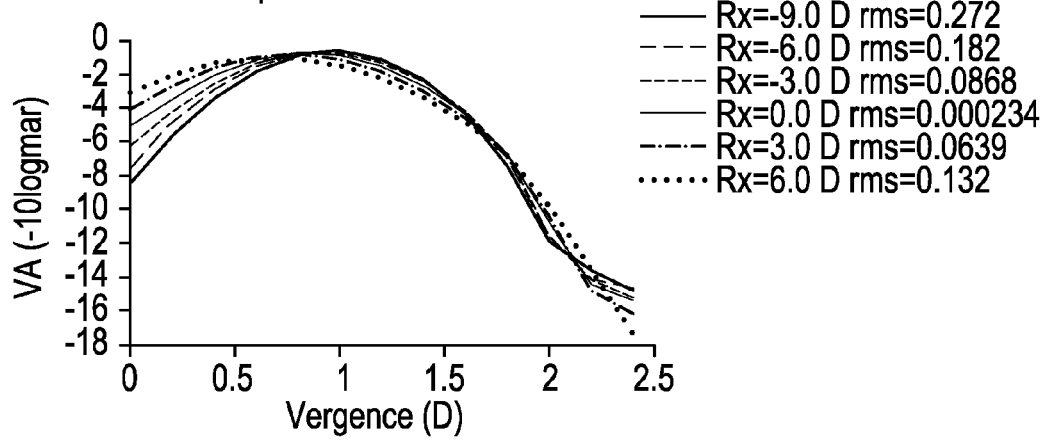
Figure 20A:
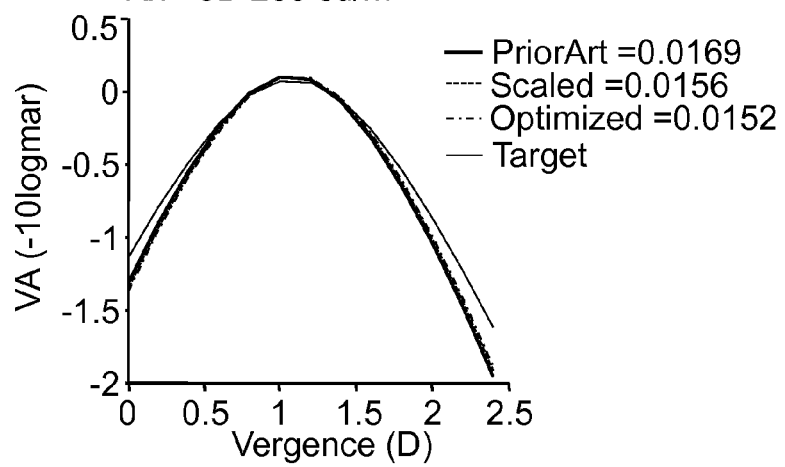
FIGS. 20-22 are simplified replots of the data illustrated in FIG. 19.
Figure 20B:
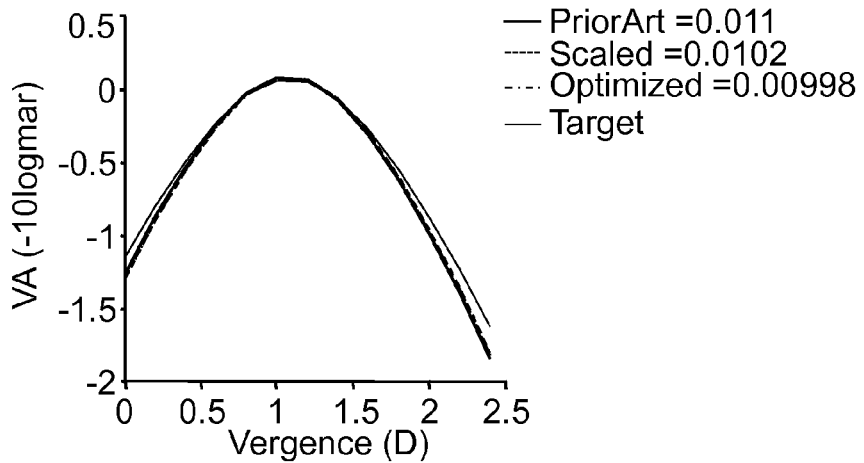
Figure 20C:
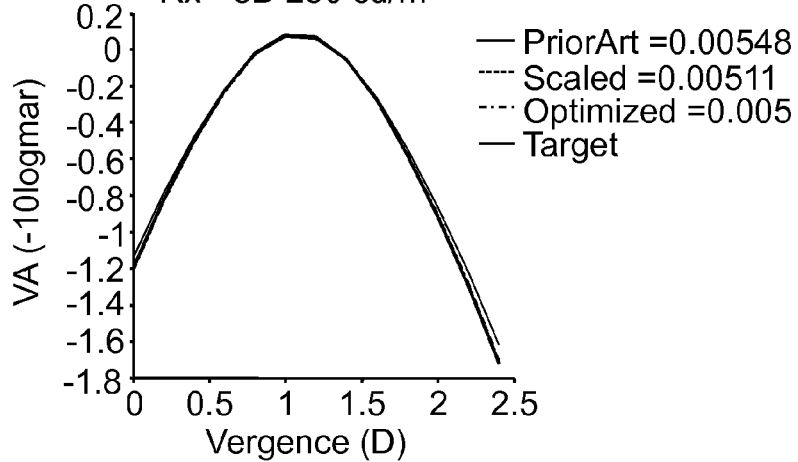
Figure 20D:
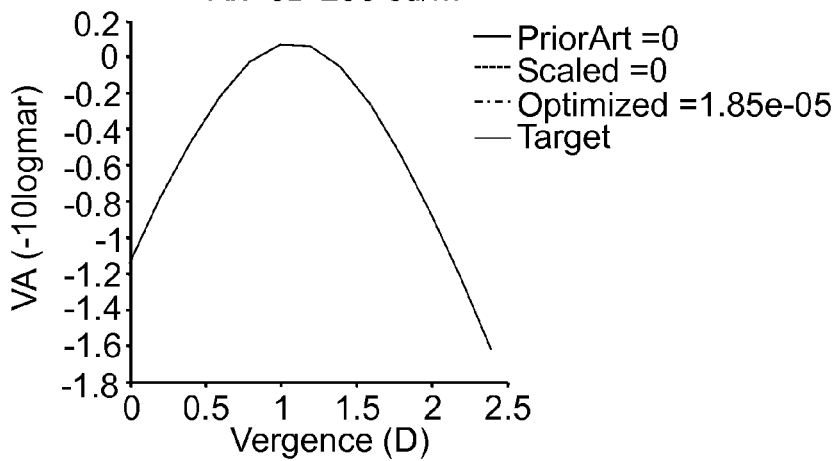
Figure 20E:
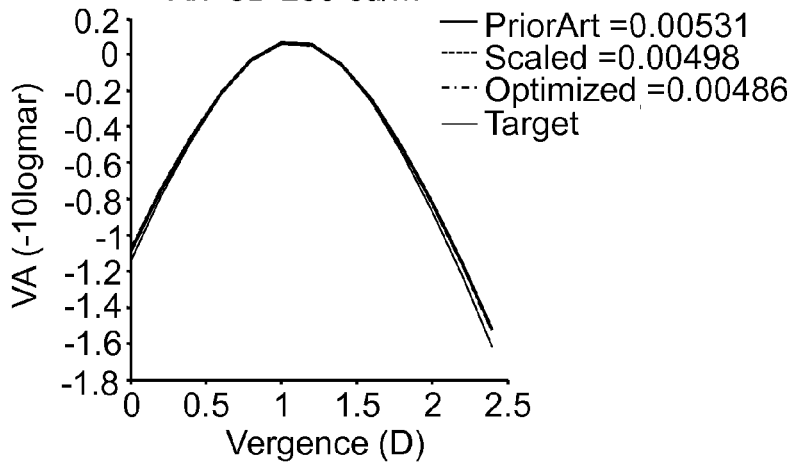
Figure 20F:
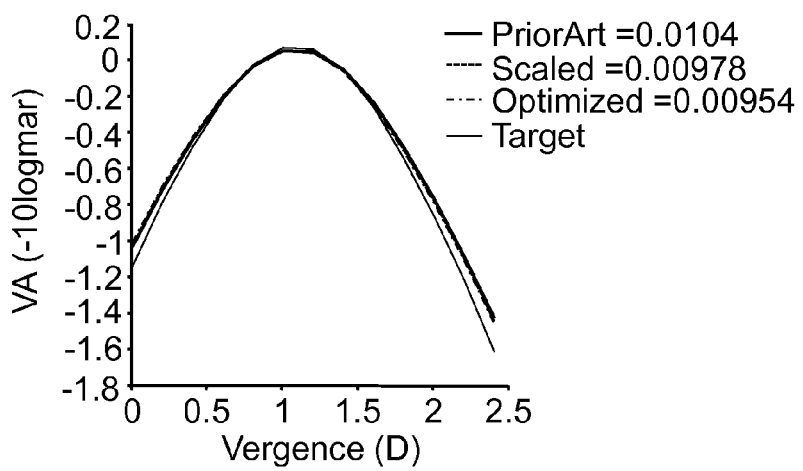
Figure 21A:
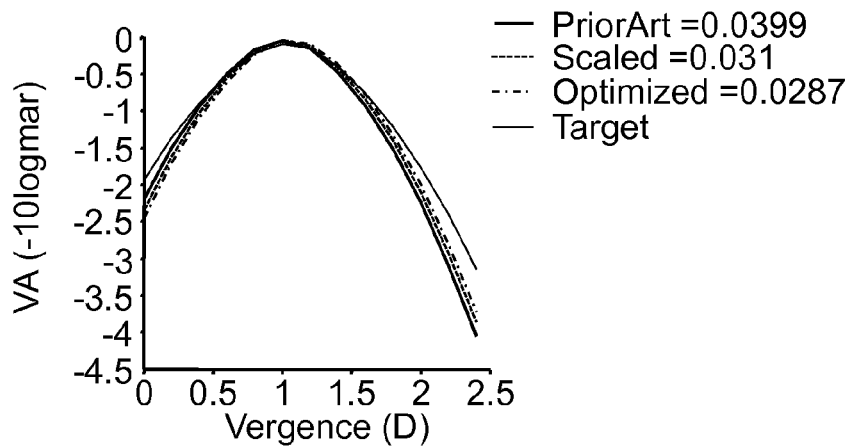
Figure 21B:
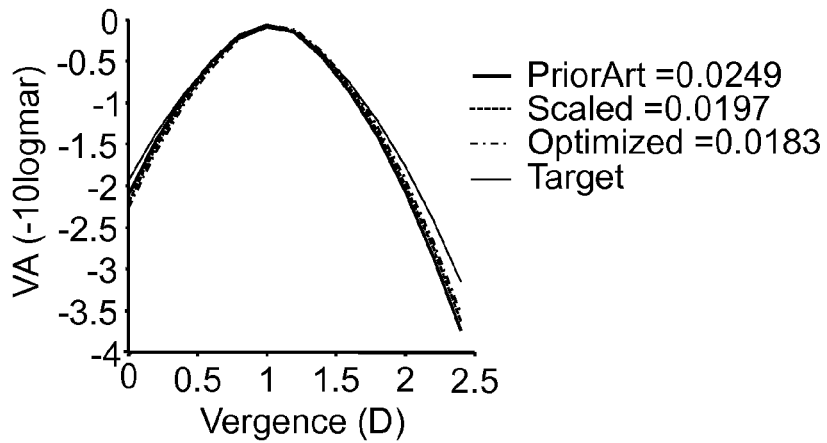
Figure 21C:
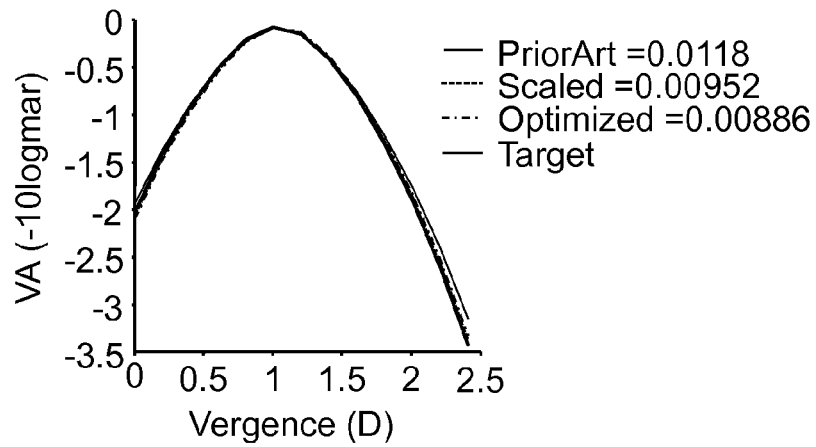
Figure 21D:
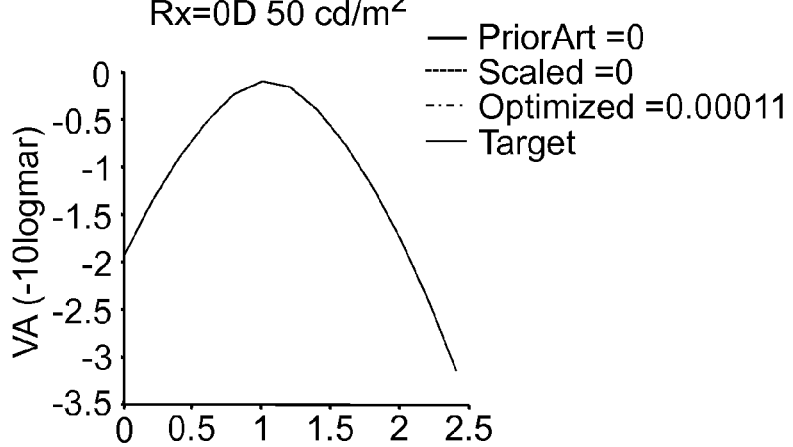
Figure 21E:
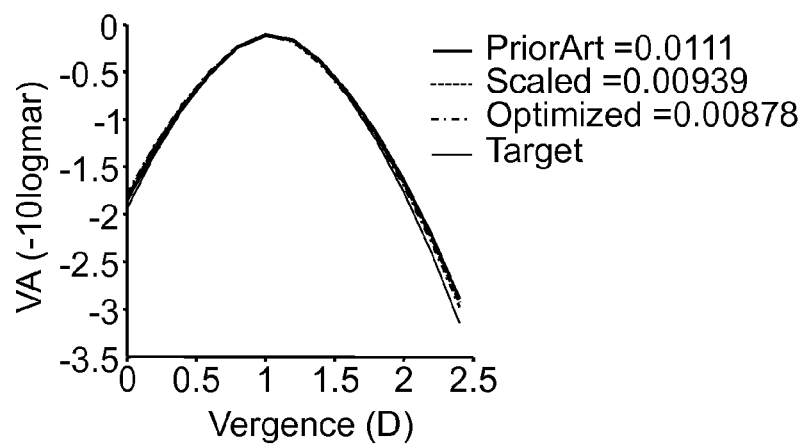
Figure 21F:
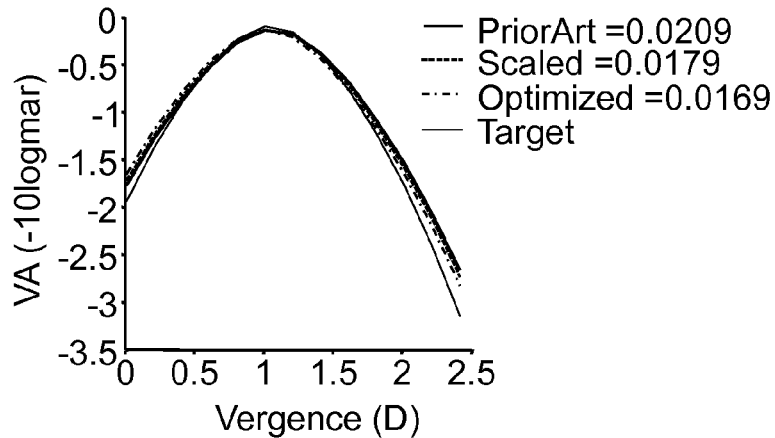
Figure 22A:
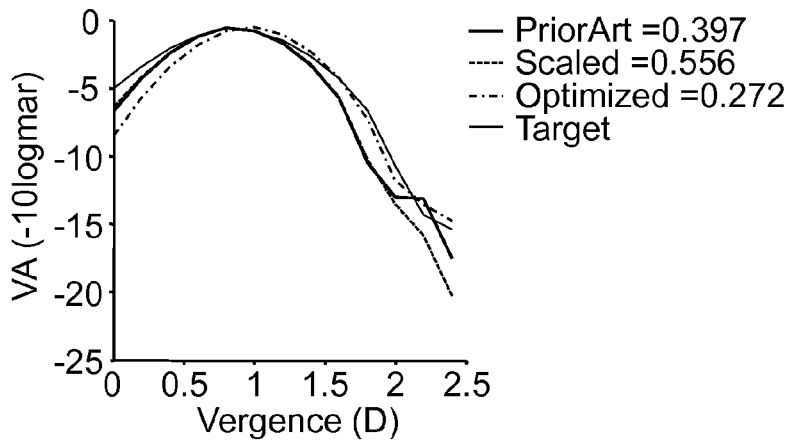
Figure 22B:
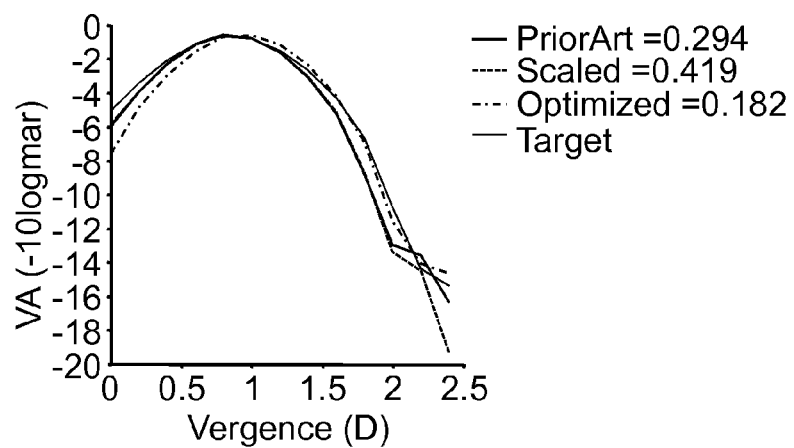
Figure 22C:
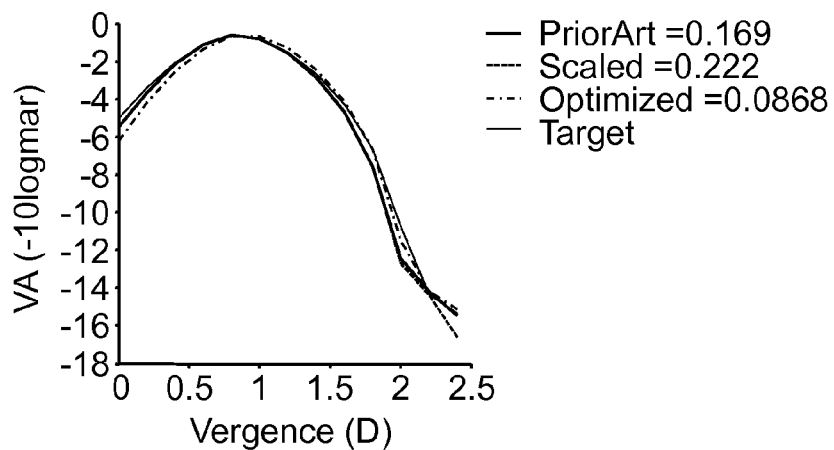
Figure 22D:
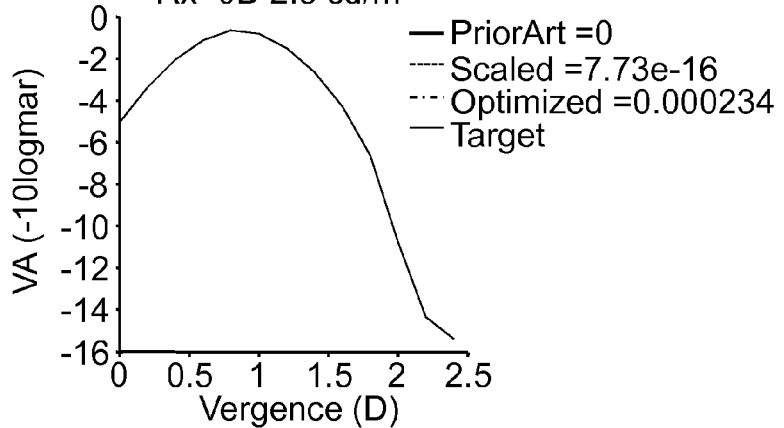
Figure 22E:
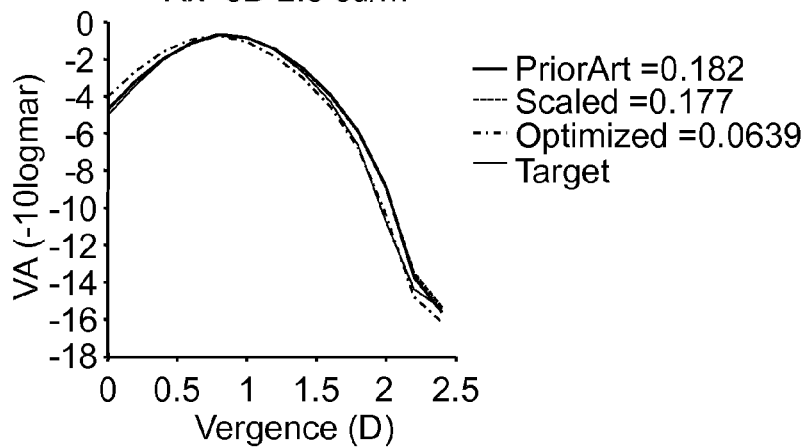
Figure 22F:
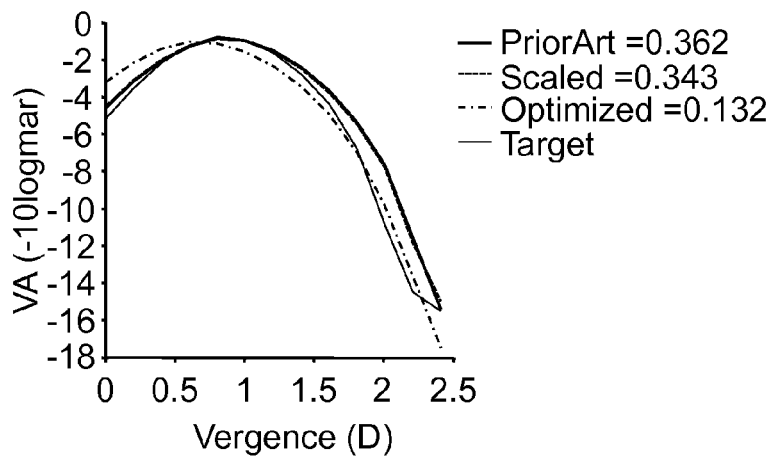

In a second example, a progressive multi-focal lens design is utilized to illustrate the results of the different methods. The nominal power profile for the progressive multi-focal lens design at $Rx_{nominal}$=0 is illustrated in FIG. 15. Applying the same magnification factor as in the previous example, the resulting designs using the scaling method are illustrated in FIG. 16. Because it is difficult to observe in FIG. 16 the scaling of the presbyopic features in the design, the same designs are replotted in FIG. 17 with the Rx subtracted from each. The results using the optimization method are illustrated in FIG. 18. The through focus VA results comparing the prior art, the scaling method, and the optimization method are illustrated in FIGS. 19-22. The RMS values showing the difference in through focus VA (via model) between the target values and the design values are summarized in Table 2.

TABLE 2

|  | Pupil | Prior | Scaled | Optimized |
|---|---|---|---|---|
| Rx = −9 D |  |  |  |  |
| EPD | 2.8 | 0.017 | 0.018 | 0.016 |
| EPD | 3.6 | 0.036 | 0.029 | 0.025 |
| EPD | 5.8 | 0.401 | 0.336 | 0.349 |
| Rx = −6 D |  |  |  |  |
| EPD | 2.7 | 0.011 | 0.012 | 0.009 |
| EPD | 3.5 | 0.023 | 0.018 | 0.017 |
| EPD | 5.7 | 0.298 | 0.256 | 0.200 |
| Rx = −3 D |  |  |  |  |
| EPD | 2.7 | 0.005 | 0.006 | 0.005 |
| EPD | 3.4 | 0.011 | 0.008 | 0.008 |
| EPD | 5.5 | 0.145 | 0.135 | 0.104 |
| Rx = 0 D |  |  |  |  |
| EPD | 2.6 | 0.000 | 0.000 | 0.000 |
| EPD | 3.3 | 0.000 | 0.000 | 0.000 |
| EPD | 5.3 | 0.000 | 0.000 | 0.000 |
| Rx = 3 D |  |  |  |  |
| EPD | 2.5 | 0.005 | 0.006 | 0.005 |
| EPD | 3.2 | 0.011 | 0.008 | 0.008 |
| EPD | 5.1 | 0.145 | 0.128 | 0.100 |
| Rx = 6 D |  |  |  |  |
| EPD | 2.4 | 0.009 | 0.012 | 0.009 |
| EPD | 3.1 | 0.021 | 0.016 | 0.015 |
| EPD | 4.9 | 0.256 | 0.231 | 0.177 |

Figure 23:
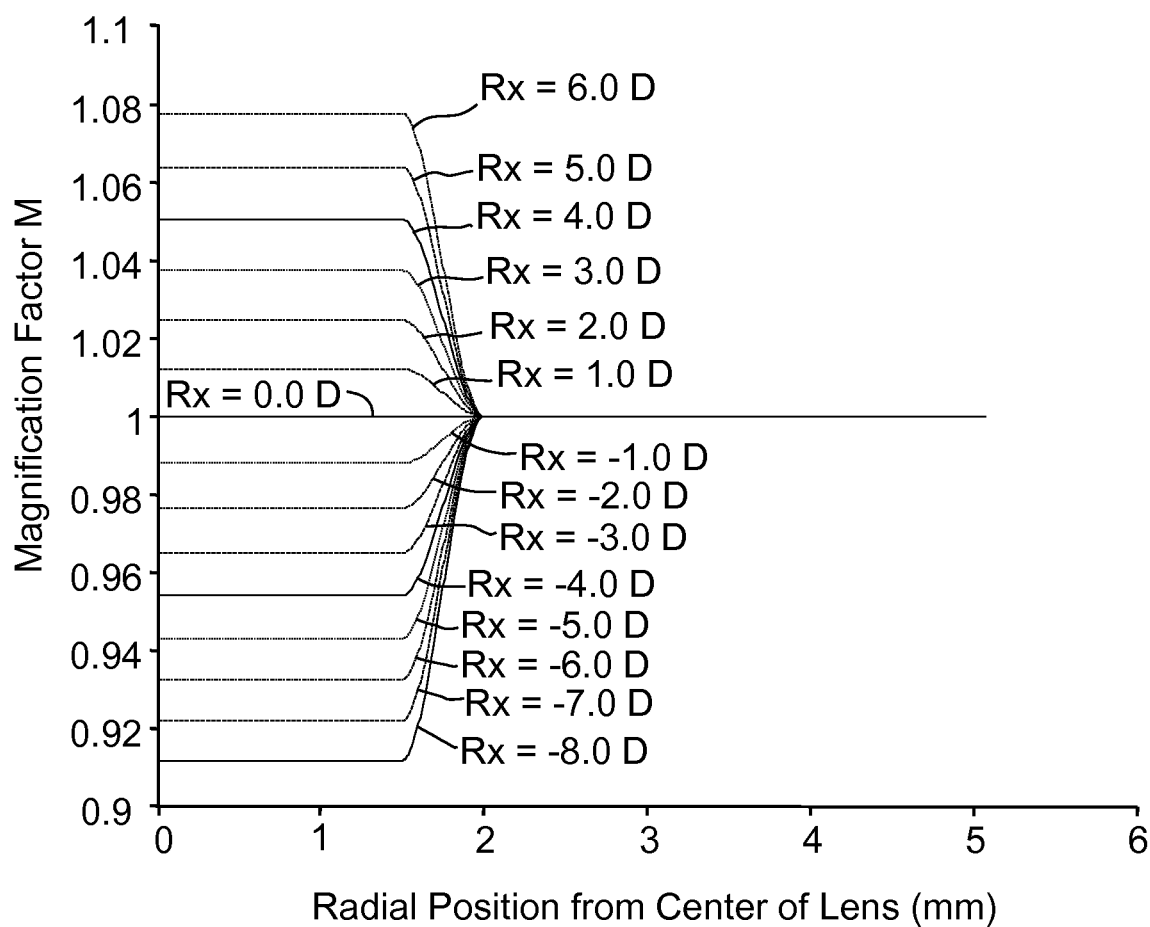
FIG. 23 is a graphical representation of magnification factor as a function of radial position for different Rx values.
Figure 24:
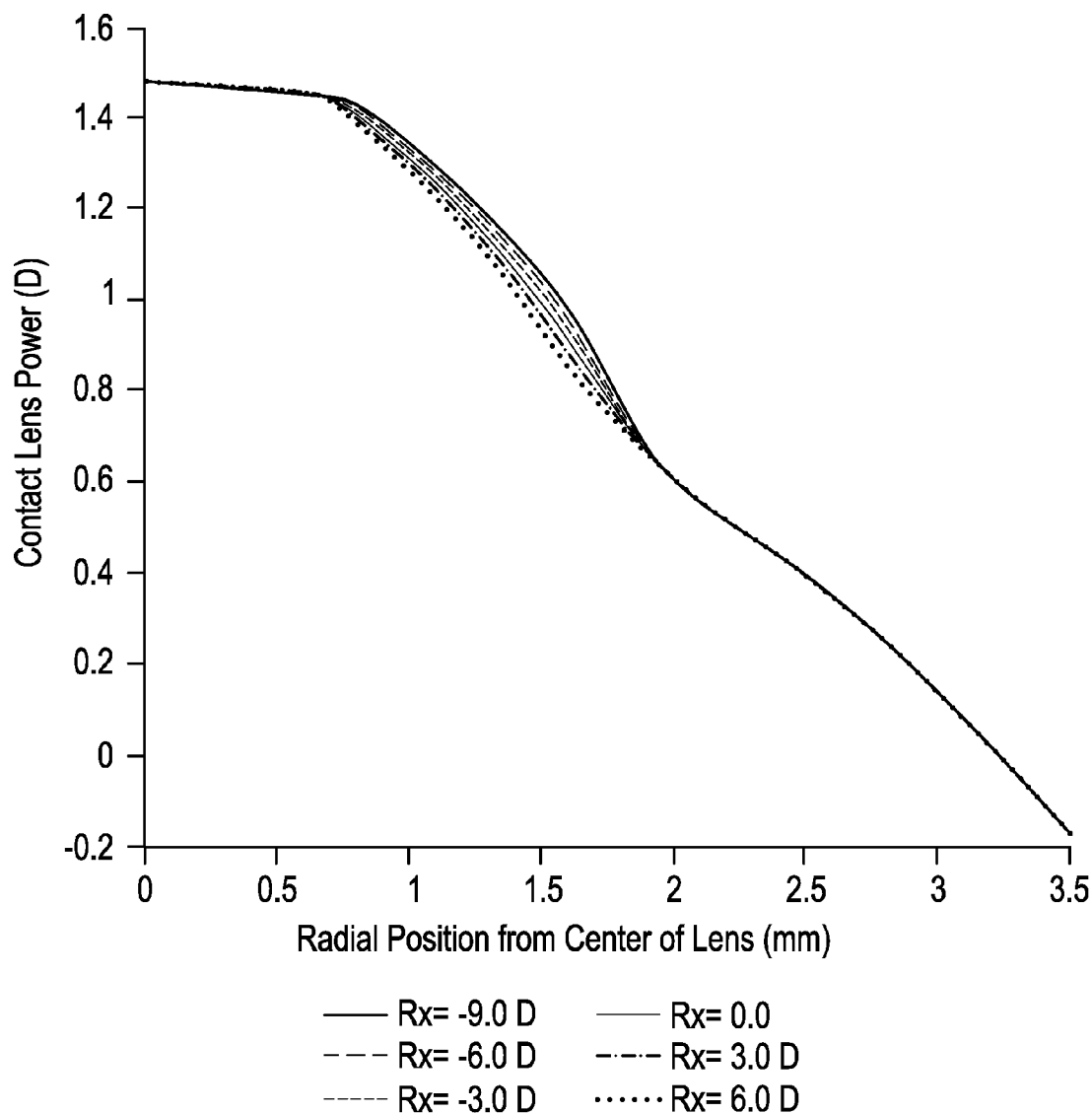
FIG. 24 is a graphical representation of power profiles for a family of lenses created utilizing a scaling method with the magnification factor M altered as shown in FIG. 23.

In accordance with another exemplary embodiment, the results of the second example may be refined. In this exemplary embodiment, the magnification factor M may be adjusted so that it is no longer constant with radial position. Adjusting the magnification factor with lens radius is useful when it is desired at or near the periphery of the lens that the design features be constant across SKUs. This could be for vision reasons, but more likely for mechanical considerations. FIG. 23 illustrates the magnification factor M as a function of radial position. In the central portion of the aperture, the M is the same as in the previous example. Beyond a radius of 2 mm the factor M is equal to one. There is an approximately 0.5 mm transition region. FIG. 24 shows the power profiles for a family of designs created using the scaling method with the magnification factor M altered as shown in FIG. 23.

The present invention is for both a method of design and the resulting lens designs that provide an improved lens for presbyopes that is designed for a particular set of pupil sizes at low, medium, and bright luminance levels to be scaled and to be used on a subject with a different pupil size response to low, medium, and bright luminance levels. In particular, it is known that pupil sizes change with ametropia (as measured by sphere Rx) so therefore this method may be applied to any design that is intended to be used on a general population where the design is done for the "average" eye. In this case the "average" eye changes with Rx so the design is adjusted by Rx using either the scaling method or the optimization method to provide improved performance relative to the prior art.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for improving ophthalmic lenses for the treatment of presbyopia, the method comprising the steps of:
   creating a base optical design with predetermined features for a lens for treating presbyopia;
   determining the power profile of the base optical design, $P_{nominal}$; and
   scaling the radial location of the predetermined features within the base optical design in proportion to the population average pupil size for the degree of ametropia of a target individual by determining a magnification factor M that relates the pupil sizes at a range of luminance levels for the ametropia level of the base design to the pupil sizes for the same luminance levels for the population average at the targeted degree of ametropia; and
   scaling the power profile of the base design, $P_{nominal}$, according to the following equations to obtain the power profile at the prescribed prescription, Rx, or degree of ametropia, $$P_2(r) = P_{nominal}(r) + SA_{eye} * r^2 + Rx - RX_{nominal}, \text{ and}$$

$$P_{Rx}(r) = P_2(M*r) - SA_{eye} * r^2,$$

wherein $SA_{eye}$ is the spherical aberration and r is the radial distance from the center of the lens.

2. The method for improving ophthalmic lenses for the treatment of presbyopia according to claim 1, wherein the step of creating a base optical design comprises creating a concentric ring design.

3. The method for improving ophthalmic lenses for the treatment of presbyopia according to claim 1, wherein the step of creating a base optical design comprises creating a continuous power profile design.

4. The method for improving ophthalmic lenses for the treatment of presbyopia according to claim 1, wherein the step of creating a base optical design comprises creating an aspheric surface design.

5. A method for improving ophthalmic lenses for the treatment of presbyopia, the method comprising the steps of:
   creating a base optical design with predetermined features for a lens for treating presbyopia;
   determining the power profile of the base optical design, $P_{nominal}$; and
   scaling the radial location of the predetermined features within the base optical design in proportion to a measured pupil size of an individual by determining a magnification factor M that relates the pupil sizes at a range of luminance levels for the ametropia level of the base design to the measured pupil size for the same luminance of the individual; and
   scaling the power profile of the base design, $P_{nominal}$, according to the following equations to obtain the power profile at the prescribed prescription, Rx, or degree of ametropia, $$P_2(r) = P_{nominal}(r) + SA_{eye} * r^2 + Rx - RX_{nominal}, \text{ and}$$

$$P_{Rx}(r) = P_2(M*r) - SA_{eye} * r^2,$$

wherein $SA_{eye}$ is the spherical aberration and r is the radial distance from the center of the lens.

6. The method for improving ophthalmic lenses for the treatment of presbyopia according to claim 5, wherein the step of creating a base optical design comprises creating a concentric ring design.

7. The method for improving ophthalmic lenses for the treatment of presbyopia according to claim 5, wherein the step of creating a base optical design comprises creating a continuous power profile design.

8. The method for improving ophthalmic lenses for the treatment of presbyopia according to claim 5, wherein the step of creating a base optical design comprises creating an aspheric surface design.

9. A method for improving ophthalmic lenses for the treatment of presbyopia, the method comprising the steps of:
   creating a base optical design with predetermined features for a lens for treating presbyopia by;
   determining the power profile of the base optical design, $P_{nominal}$; and
   scaling the radial location of the predetermined features within the base optical design in proportion to the population average pupil size for the degree of ametropia of a target individual by determining magnification factor factors $M_1$ through $M_n$ that relates the pupil sizes at a range of luminance levels for the ametropia level of the base design to the pupil sizes for the same luminance levels for the population average at the targeted degree of ametropia; and
   scaling the power profile of the base design, $P_{nominal}$, according to the following equations to obtain the power profile at the prescribed prescription, Rx, or degree of ametropia, $$P_2(r) = P_{nominal}(r) + SA_{eye} * r^2 + Rx - RX_{nominal}, \text{ and}$$

$$P_{RX}(r) = P_2(M_1 * r + M_2 * r^2 + \ldots) - SA_{eye} * r^2,$$

wherein $SA_{eye}$ is the spherical aberration and r is the radial distance from the center of the lens.

10. The method for improving ophthalmic lenses for the treatment of presbyopia according to claim 9, wherein the step of creating a base optical design comprises creating a concentric ring design.

11. The method for improving ophthalmic lenses for the treatment of presbyopia according to claim 9, wherein the step of creating a base optical design comprises creating a continuous power profile design.

12. The method for improving ophthalmic lenses for the treatment of presbyopia according to claim 9, wherein the step of creating a base optical design comprises creating an aspheric surface design.

13. A method for improving ophthalmic lenses for the treatment of presbyopia, the method comprising the steps of:
   creating a base optical design with predetermined features for a lens for treating presbyopia;
   determining the power profile of the base optical design, $P_{nominal}$; and
   scaling the radial location of the predetermined features within the base optical design in proportion to a measured pupil size of an individual by determining magnification factors $M_1$ through $M_n$ that relates the pupil sizes at a range of luminance levels for the ametropia level of the base design to the measured pupil size for the same luminance of the individual; and
   scaling the power profile of the base design, $P_{nominal}$, according to the following equations to obtain the power profile at the prescribed prescription, Rx, or degree of ametropia, $$P_2(r) = P_{nominal}(r) + SA_{eye} * r^2 + Rx - RX_{nominal}, \text{ and}$$

$$P_{RX}(r) = P_2(M_1 * r + M_2 * r^2 + \ldots) - SA_{eye} * r^2,$$

wherein $SA_{eye}$ is the spherical aberration and r is the radial distance from the center of the lens.

14. The method for improving ophthalmic lenses for the treatment of presbyopia according to claim 13, wherein the step of creating a base optical design comprises creating a concentric ring design.

15. The method for improving ophthalmic lenses for the treatment of presbyopia according to claim 13, wherein the step of creating a base optical design comprises creating a continuous power profile design.

16. The method for improving ophthalmic lenses for the treatment of presbyopia according to claim 13, wherein the step of creating a base optical design comprises creating an aspheric surface design.

* * * * *